United States Patent
Walters et al.

(10) Patent No.: US 8,002,756 B2
(45) Date of Patent: Aug. 23, 2011

(54) METHOD AND APPARATUS FOR DELIVERING A THERAPEUTIC SUBSTANCE THROUGH AN INJECTION PORT

(75) Inventors: Michael R. Walters, Baltimore, MD (US); Bradley S. Thomas, Timonium, MD (US); Katherine Stanton, Pompton Lakes, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 11/948,804

(22) Filed: Nov. 30, 2007

(65) Prior Publication Data
US 2009/0082734 A1 Mar. 26, 2009

Related U.S. Application Data

(60) Provisional application No. 60/873,580, filed on Dec. 8, 2006.

(51) Int. Cl.
*A61M 5/32* (2006.01)
*A61M 5/00* (2006.01)
*A61B 19/00* (2006.01)

(52) U.S. Cl. ........ 604/263; 604/192; 604/403; 604/198; 604/199

(58) Field of Classification Search ............. 604/165.01, 604/166.01, 513, 240, 288.01, 174, 192–199, 604/110, 115–117, 403, 163, 263; 403/181, 403/344, 52; 16/302, 366, 367, 225, 2.1, 16/336
See application file for complete search history.

(56) References Cited

U.S. PATENT DOCUMENTS

| | | | | |
|---|---|---|---|---|
| 4,559,043 A | * | 12/1985 | Whitehouse et al. | 604/201 |
| 4,675,006 A | | 6/1987 | Hrushesky | |
| 4,755,173 A | | 7/1988 | Konopka et al. | |
| 4,966,588 A | | 10/1990 | Rayman et al. | |
| 5,257,980 A | | 11/1993 | Van Antwerp et al. | |
| 5,486,163 A | * | 1/1996 | Haynes | 604/192 |
| 5,504,973 A | * | 4/1996 | Kameyama | 16/2.1 |
| 5,545,143 A | | 8/1996 | Fischell | |
| 5,688,254 A | * | 11/1997 | Lopez et al. | 604/535 |
| 5,925,032 A | * | 7/1999 | Clements | 606/1 |

(Continued)

FOREIGN PATENT DOCUMENTS
EP 0 856 331 A2 8/1998
(Continued)

*Primary Examiner* — Matthew F Desanto
(74) *Attorney, Agent, or Firm* — Alan W. Fiedler; Roylance, Abrams, Berdo and Goodman LLP

(57) ABSTRACT

Adapters for utilizing a syringe or pen injector with a subcutaneous injection port to deliver a therapeutic substance through the injection port and methods of using the adapters are provided. A syringe adapter has a body having a first end and a second end. The first end of the body is configured to receive and engage the end of a syringe so that the cannula of the syringe is held at a fixed position with the respect to the adapter. The second end of the adapter configured to mate with a mating portion of the injection port. When the second end of the adapter engages the mating portion of the injection port, the adapter assures that the cannula of the syringe is properly aligned with the subcutaneous injection port and assures that the cannula penetrates the injection port to the proper depth. Adapters for use with pen style delivery systems are also disclosed. Additionally, an adapter to facilitate loading a syringe with a therapeutic substance from a vial is disclosed.

20 Claims, 23 Drawing Sheets

U.S. PATENT DOCUMENTS

| | | | |
|---|---|---|---|
| 6,017,328 A | 1/2000 | Fischell et al. | |
| 6,074,371 A | 6/2000 | Fischell | |
| 6,096,024 A * | 8/2000 | Graves et al. | 604/535 |
| 6,213,978 B1 | 4/2001 | Voyten | |
| 6,261,266 B1 * | 7/2001 | Jepson et al. | 604/201 |
| 6,494,865 B1 * | 12/2002 | Alchas | 604/192 |
| 6,830,562 B2 | 12/2004 | Mogensen et al. | |
| 6,923,791 B2 | 8/2005 | Douglas | |
| 7,115,112 B2 | 10/2006 | Mogensen et al. | |
| 7,594,910 B2 * | 9/2009 | Butts et al. | 604/533 |
| 2004/0006316 A1 | 1/2004 | Patton | |
| 2005/0101932 A1 | 5/2005 | Cote et al. | |
| 2005/0209581 A1 * | 9/2005 | Butts et al. | 604/523 |
| 2007/0106229 A1 * | 5/2007 | Wong | 604/249 |
| 2008/0215003 A1 | 9/2008 | Kornerup | |

FOREIGN PATENT DOCUMENTS

| | | |
|---|---|---|
| EP | 0 903 157 | 3/1999 |
| WO | 2006/099441 | 9/2006 |

* cited by examiner

METHOD AND APPARATUS FOR DELIVERING A THERAPEUTIC SUBSTANCE THROUGH AN INJECTION PORT

CROSS REFERENCE TO RELATED APPLICATION

This application claims the benefit under 35 U.S.C. §119 (e) of provisional application Ser. No. 60/873,580, filed Dec. 8, 2006, the entire disclosure of which is hereby incorporated by reference.

FIELD OF THE INVENTION

The present invention relates to the delivery of therapeutic substances through injection ports. More particularly, the present invention relates to a method and apparatus for using a syringe or pen injector to deliver a therapeutic substance through a subcutaneous injection port.

BACKGROUND

Therapeutic substances are often delivered by subcutaneous injection. One common device used to facilitate the delivery of such substances is a subcutaneous injection port. Subcutaneous injection ports typically include a housing with a soft tubular cannula and an apparatus for delivering a therapeutic substance to the cannula. To use such a port, a puncturing device such as a rigid needle is used to place the soft cannula in the subcutaneous tissue. The rigid needle is then withdrawn and the cannula and housing are left at the infusion site. A therapeutic substance may then be introduced through the cannula. This type of subcutaneous injection port may be left in a patient for several days. Examples of subcutaneous injection ports are disclosed in U.S. Pat. No. 6,074,371 to Fischell, and U.S. Pat. No. 6,017,328 to Fischell, which are hereby incorporated by reference in their entirety.

A subcutaneous injection port may be used to deliver a bolus of medicine with a syringe. A subcutaneous injection port suitable for use with a syringe is disclosed in U.S. Patent Publication No. 2004/0006316 A1 to Patton, which is hereby incorporated by reference in its entirety.

One problem that may occur when injecting therapeutic substances into a subcutaneous injection port with a syringe is misalignment between the cannula of the syringe and the injection port. If there is too much misalignment, the injection port may be damaged or improper dosages may be delivered. Furthermore, a user may completely miss the injection port, and accidentally stick themselves with the cannula.

Accordingly, there is a need for an improved apparatus for delivering therapeutic substances into a subcutaneous injection port.

SUMMARY OF THE INVENTION

An aspect of the present invention is to address at least the above problems and/or disadvantages and to provide at least the advantages described below. Accordingly, an aspect of the present invention is to provide an adapter for aligning a cannula of a syringe or pen injection with an injection port, such as a subcutaneous injection port.

Another aspect of the present invention is to provide an adapter for controlling the depth of penetration of a cannula of a syringe or pen injection needle into an injection port, such as a subcutaneous injection port.

Yet another aspect of the present invention is to provide an adapter that shields a cannula of a syringe or pen needle to prevent accidental needle punctures.

In accordance with an aspect of the present invention, an adapter for utilizing a syringe with an injection port, such as a subcutaneous injection port, is provided. The adapter has a body having a first end and a second end. The first end of the body is adapted to receive an end of a syringe. The second end of the adapter is adapted to mate with the injection port. The adapter aligns the cannula of the syringe with the injection port and controls the depth of penetration of the cannula.

In accordance with another aspect of the present invention, an adapter for utilizing a pen delivery system with an injection port, such as a subcutaneous injection port, comprises an outer shield and a pen needle disposed in the outer shield. The outer shield has a first end and a second end. The first end of the outer shield is configured to mate with a pen delivery system. The second end of the outer shield is configured to mate with an injection port. The adapter aligns the pen needle with the injection port and controls the depth of penetration of the pen needle.

In accordance with another aspect of the present invention, an adapter for utilizing a pen delivery system with an injection port, such as a subcutaneous injection port, comprises first, second, and third legs that are connected together to form a triangular shaped body, first and second recesses formed in the first and second legs of the adapter to accommodate a pen needle assembly, and extending struts on the first and second legs that are arranged in a geometric pattern that corresponds to the shape of corresponding features on an injection port. The adapter aligns the pen needle with the injection port and controls the depth of penetration of the pen needle.

In accordance with another aspect of the present invention, a vial adapter for use with an injection port adapter comprises a disc with a bottom surface and a top surface. A plurality of flexible fingers extend from the bottom surface of the disc and have a retention flange formed on an inner surface of the fingers. The flexible fingers are configured to fit over the neck of vial, and the flexible fingers allow the retention flange to pass over a crimp ring on the neck of a vial. A cylinder extends from the top surface of the disc. The cylinder has an outside diameter that corresponds to the inner diameter of an injection port adapter. A septum covers an opening at the top of the cylinder to form a cavity within the cylinder. A cannula extends through the disc into the cavity in the cylinder.

BRIEF DESCRIPTION OF THE DRAWINGS

The above and other objects, features, and advantages of certain exemplary embodiments of the present invention will be more apparent from the following description taken in conjunction with the accompanying drawings, in which.

Throughout the drawings, the same reference numerals will be understood to refer to the same elements, features, and structures.

DETAILED DESCRIPTION OF EXEMPLARY EMBODIMENTS

The matters defined in the description such as a detailed construction and elements are provided to assist in a comprehensive understanding of the embodiments of the invention and are merely exemplary. Accordingly, those of ordinary skill in the art will recognize that various changes to and modifications of the embodiments described herein can be made without departing from the scope and spirit of the invention. Also, descriptions of well-known functions and constructions are omitted for clarity and conciseness.

Figure 1A:
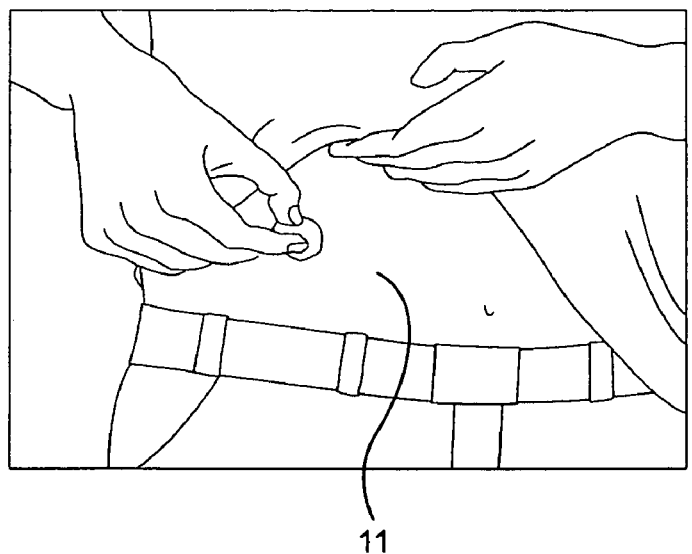
FIGS. 1A-1G are illustrations of an exemplary embodiment of an injection port and a method of using the same.
Figure 1B:
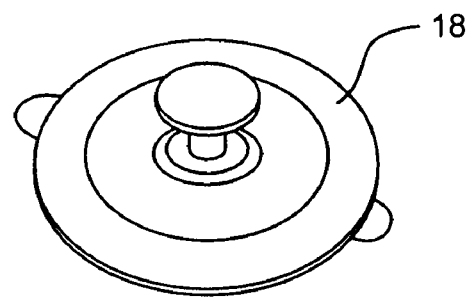
Figure 1C:
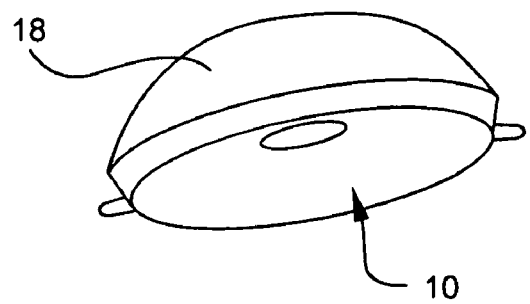
Figure 1D:
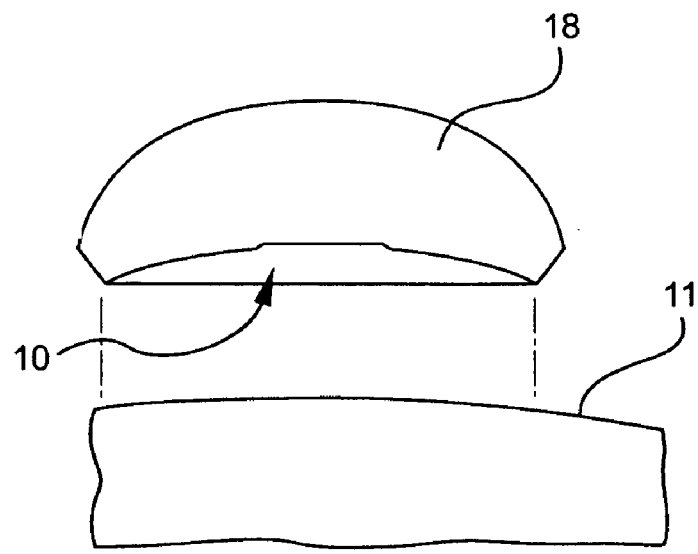
Figure 1E:
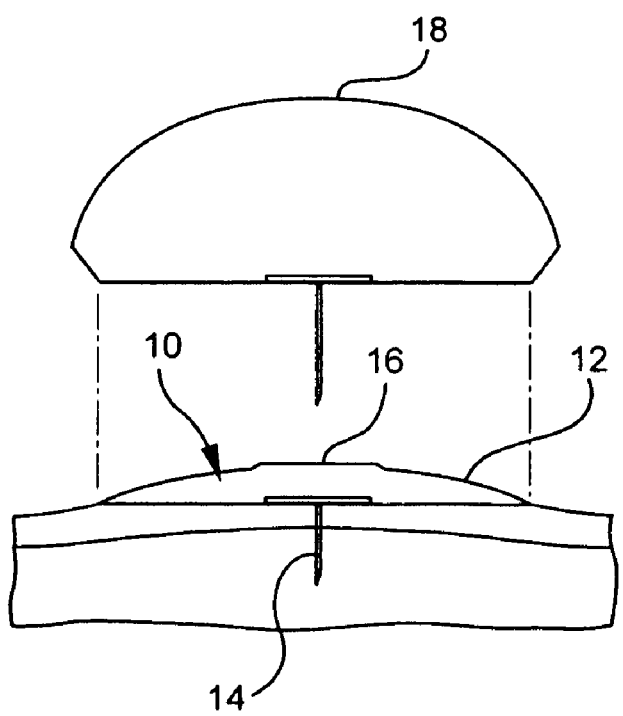
Figure 1F:
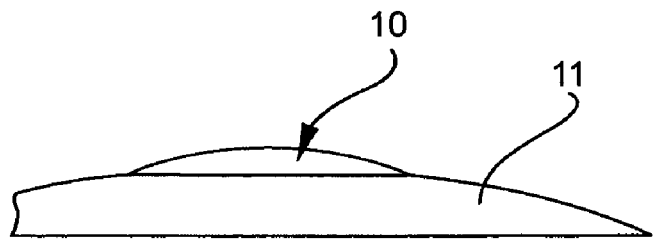
Figure 1G:
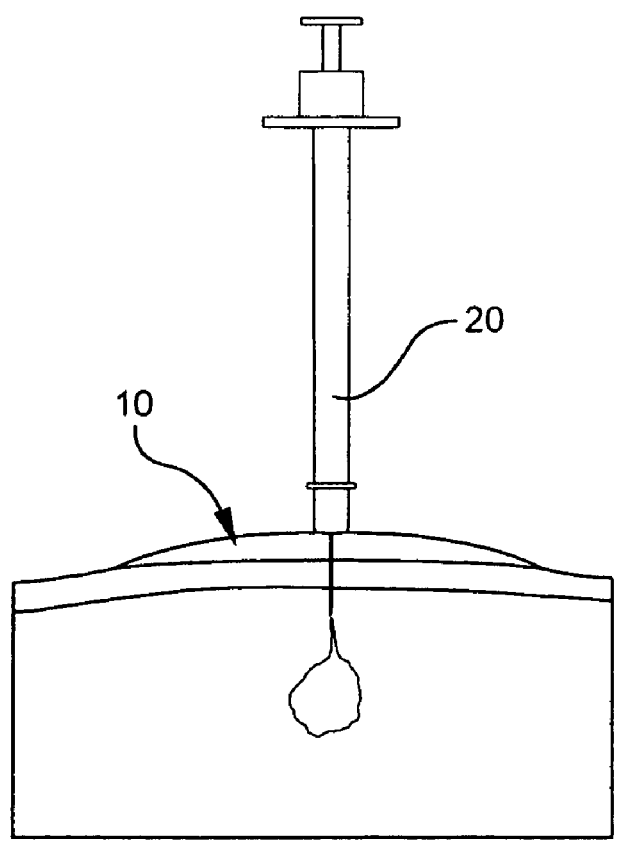
Figure 2:
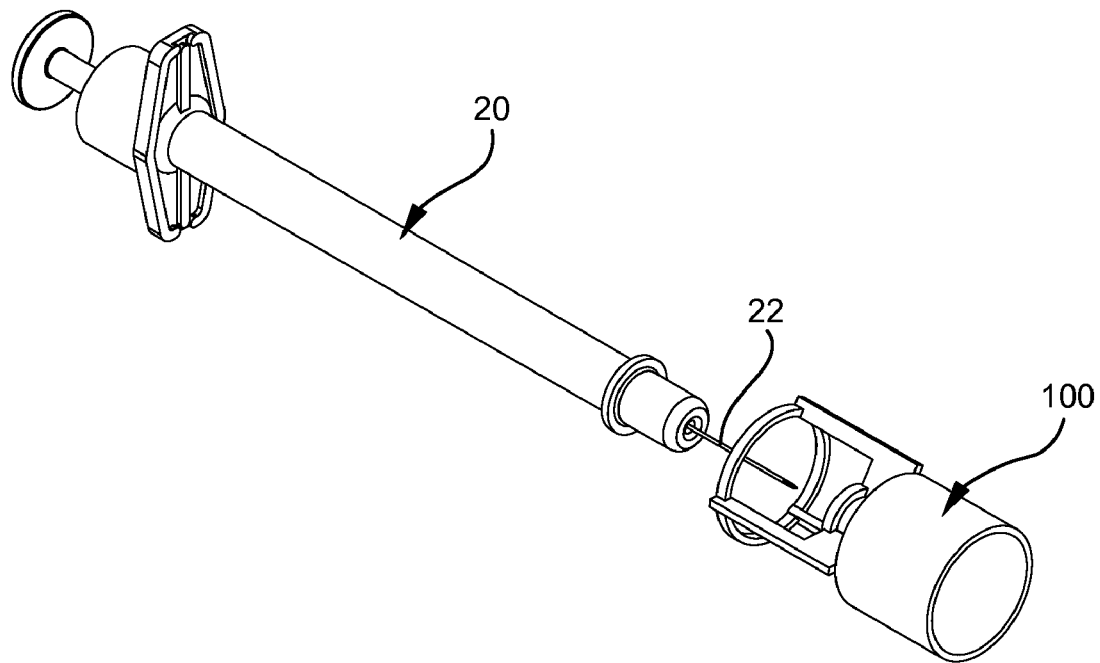
FIG. 2 is a perspective view of a syringe and an injection port adapter according to an exemplary embodiment of the present invention.
Figure 3:
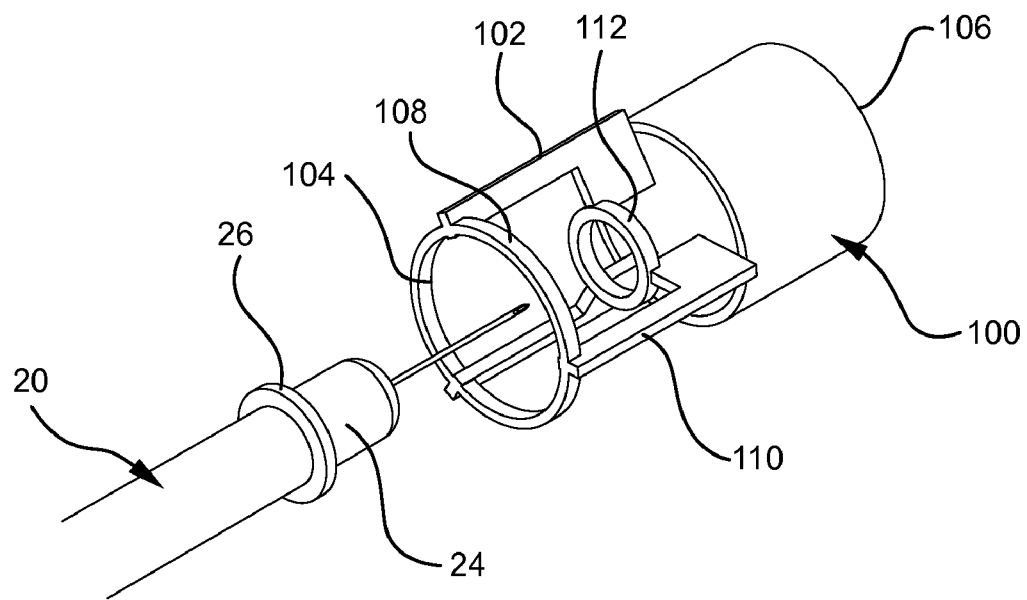
FIG. 3 is an enlarged perspective of the syringe and injection port adapter of FIG. 2, with the tip of the syringe approaching a centering ring of the adapter.
Figure 4:
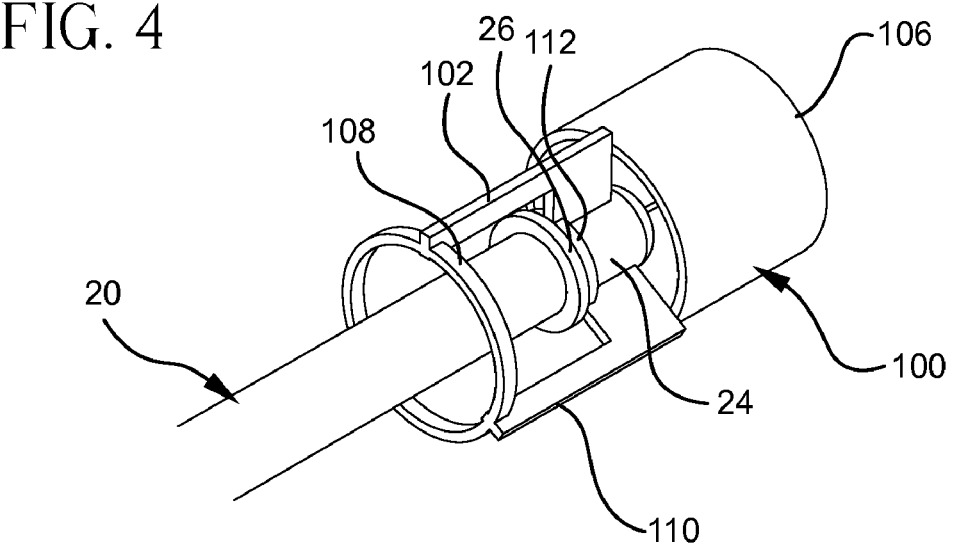
FIG. 4 is an enlarged perspective of the syringe and injection port adapter of FIG. 2, with the tip of the syringe entering the centering ring of the adapter.

Referring to FIGS. 1A-1G, a subcutaneous injection port 10 according to an exemplary embodiment of the present invention includes a body portion 12, a soft cannula (or catheter) 14, and a septum 16 that forms a hollow cavity connected to the cannula. To use the injection port, an adhesive material is placed on the lower surface of the body portion 12 of the injection port 10. The adhesive material may be adhesive tape, and the tape may be covered with a liner prior to use to prevent the tape from adhering to an unwanted surface. After the skin 11 has been cleaned and prepared (FIG. 1A), the injection port 10 is placed against a patient's skin at a desired location, and the cannula 14 is inserted into the subcutaneous tissue (FIGS. 1D, 1E and 1F). The cannula 14 is preferably inserted by an automatic insertion device 18 (FIGS. 1B and 1C), such as those available from Unomedical a/s of Birkeroed, Denmark. Suitable insertion device are disclosed in U.S. Pat. No. 6,830,562 to Mogensen et al. and U.S. Pat. No. 7,115,112 to Mogensen et al., both of which are hereby incorporated by reference in their entirety.

With the injection port in place, a therapeutic substance, such as insulin, may be injected through the injection port by utilizing a conventional syringe 20 (FIG. 1G), a conventional pen needle injection device (not illustrated), or the like. Suitable syringes are available from the assignee of the present application, Becton, Dickinson and Company of Franklin Lakes, N.J. To inject the therapeutic substance, the cannula of the syringe or pen needle is placed through the septum 16 of the injection port 10, and the therapeutic substance is discharged.

To facilitate the use of a conventional syringe with the injection port and to prevent misalignment of the cannula with the injection port, adapters that interface the syringe with the injection port may be provided. Exemplary embodiments of suitable adapters will now be described, and additional details of the injection port will be discussed as necessary in connection with the detailed description of the adapters.

FIGS. 2-5 illustrate an injection port adapter 100 according to an exemplary embodiment of the present invention. The injection port adapter 100 provides an interface between a conventional, commercially available syringe and an injection port. The injection port adapter 100 has a hollow body 102 with a first end 104 and a second end 106. The first end 104 of the hollow body 102 receives the end of the syringe 20 and guides the syringe 20 into a desired position within the hollow body 102. The second end 106 of the hollow body 102 has a geometric configuration that corresponds to a corresponding mating portion of the injection port. In this manner, as will be discussed in further detail below, the cannula 22 of the syringe 20 is guided to and held at the appropriate location with respect to the injection port.

In the illustrated embodiment, the first end 104 of the hollow body 102 is an annular, ring-shaped member 108. The inner diameter of the annular ring 108 is large enough to allow the end of the syringe to pass through and enter into the adapter.

The annular ring 108 is connected to the second end 106 of the adapter 100 by a plurality of ribs 110. In the illustrated embodiment, three ribs 110 are used to connect the annular ring to the second end 106 of the adapter 100. Any number of ribs may be used, however. A solid connection may also be used to form the connection. The use of ribs, however, minimizes the surface area of the adapter 100, and therefore minimizes the potential of the cannula 22 of the syringe 20 coming into contact with the adapter 100. Contact between the needle and a non-sterile adapter has the potential to introduce foreign bodies into the body and contaminate the needle.

Figure 5:
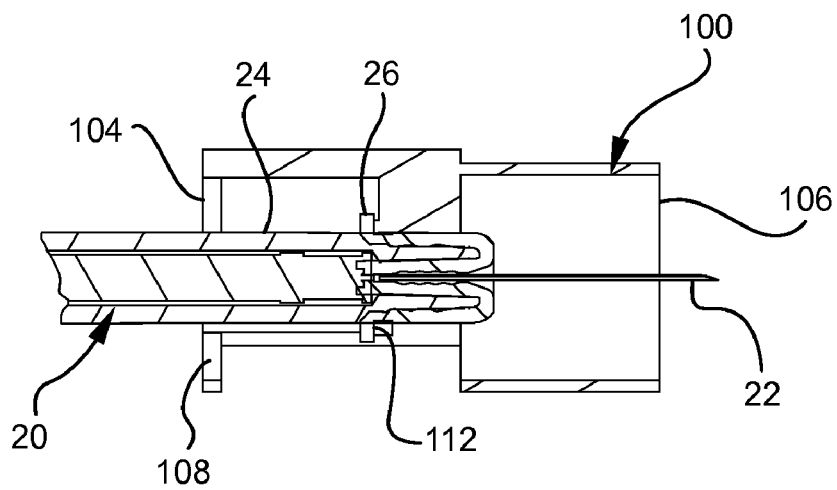
FIG. 5 is a sectional view of the syringe and the injection port adapter of FIG. 2, with the tip of the syringe in the centering ring of the adapter.
Figure 6:
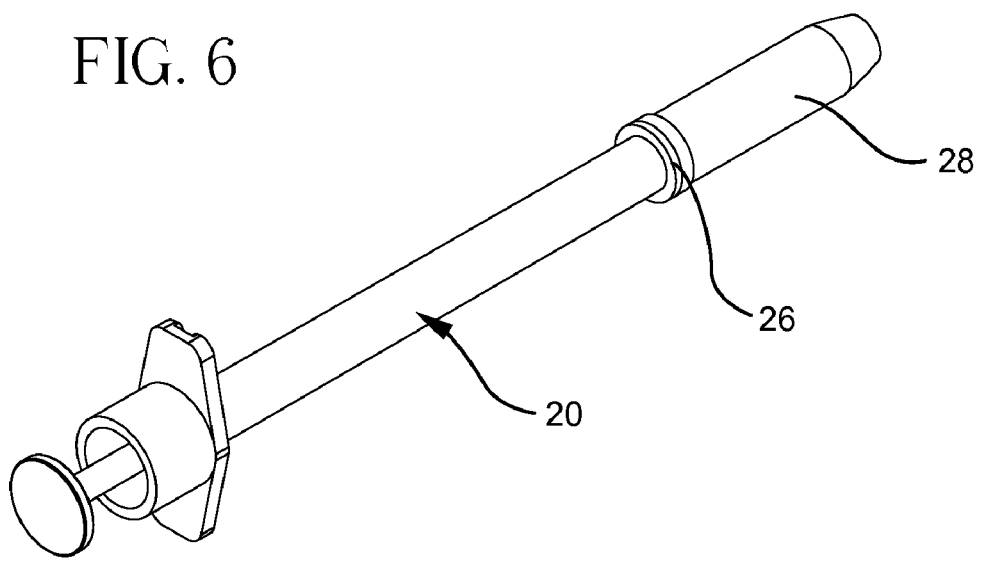
FIG. 6 is a perspective view of a syringe suitable for use with the exemplary embodiments of the present invention.

A centering ring 112 is disposed in the hollow body 102, and is supported by the plurality of ribs 110. The centering ring 112 receives the end of the syringe, and holds the end of the syringe in a stable position. Preferably, the inner diameter of the centering ring forms a friction fit with the end of the syringe to hold the adapter in place on the end of the syringe. Moreover, a syringe typically has a hub 24 with an annular flange 26 near the end of the syringe so that a sterility cap 28 may be placed on the end of the syringe (see FIG. 6). As seen in FIG. 5, when the adapter 100 is placed on the syringe 20, the annular flange 26 on the syringe 20 is pressed against the centering ring 112. Consequently, the centering ring 112 both aligns the syringe 112 with the adapter and controls the depth of the insertion of the cannula 22.

The adapter 100 may be formed of any suitable material, such as polypropylene. The adapter 100 may be formed by any conventional manufacturing method, including injection molding and the like.

To use the adapter 100 to make an injection of a therapeutic substance through an injection port, a user removes the sterility cap 28 from a syringe 20. The syringe 20 may be pre-loaded with a therapeutic substance. More typically, however, a user will load the syringe 20 with a dose of a therapeutic substance contained in a separate container, such as a vial, in a conventional manner. The user may then move the end of the loaded syringe 20 through the annular ring 108 of the adapter 100 and into the centering ring 112 until the annular flange 26 of the syringe 20 abuts the centering ring 112. The syringe 20 and adapter are now ready for use. At this point, it should be noted that the cannula is recessed within the adapter so that accidental punctures are minimized.

Figure 7:
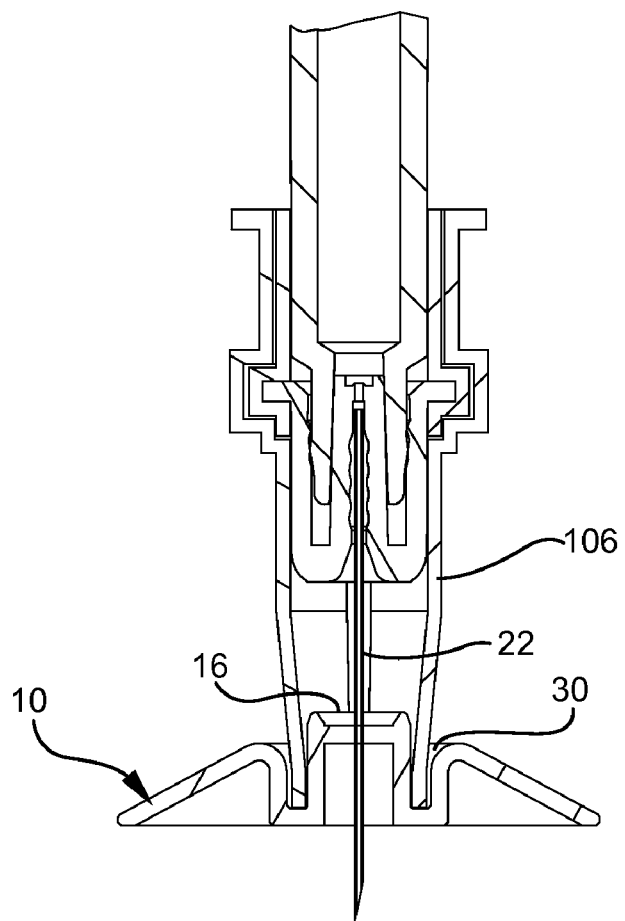
FIG. 7 is a sectional view of the second end of the syringe and injection port adapter of FIG. 2 mated with an injection port.
Figure 8:
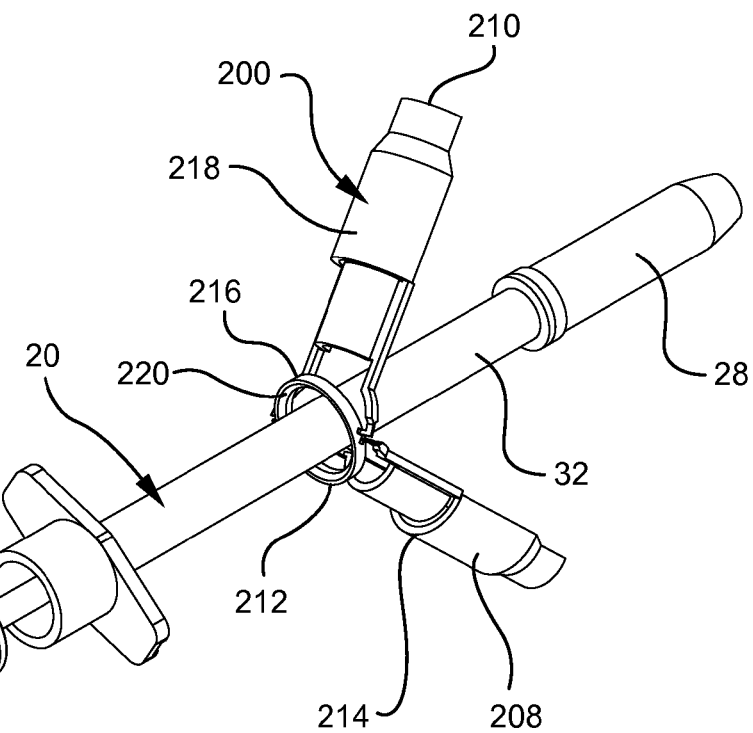
FIG. 8 is a perspective view of a syringe and an injection port adapter according to another exemplary embodiment of the present invention.

The syringe 20 and the attached adapter 100 are then brought to the injection port 10. As seen in FIG. 7, the injection port 10 has a mating portion 30 for engaging the second end 106 of the injection port adapter 100. In the illustrated exemplary embodiment, the mating portion 30 is an annular recess. The second end 106 of the injection port adapter 100 is placed into the mating portion 30 and engages the mating portion 30 so that the injection port adapter 100 is held in a stable manner. Although the second end 106 of the adapter 100 and the corresponding mating portion 30 are annular in the illustrated exemplary embodiment, other shapes may be used if desired.

When the injection port adapter 100 is placed into the mating portion on the injection port 10, the cannula 22 pierces the septum 16 of the injection port 10, and the engagement of the mating portion 30 and the second end 106 of the adapter 100 assures that the cannula 22 is placed at the proper depth within the injection port. After the syringe has been placed on the injection port, the syringe may be used to dispense the therapeutic substance contained in the syringe into the injection port. The therapeutic substance then travels through the soft cannula 14 of the injection port 10 and into the subcutaneous tissue.

At this point, the syringe 10 and adapter 100 assembly may be removed from the injection port. Typically, the syringe 10 will be disposed of for safety and health reasons. The adapter 100 may also be disposed of. The adapter 100, however, does not directly contact any body fluids, and may be reused if desired.

FIGS. 8-11 show a syringe 20 and an injection port adapter 200 in accordance with another exemplary embodiment of the present invention. The injection port adapter 200 of this exemplary embodiment includes a hollow body 202 with a first end 206 and a second end 204. The hollow body 202 has a first body portion 208 and a second body portion 210. The first body portion has a first attachment collar portion 212 and a first foldable portion 214 that is pivotable with respect to the first attachment collar portion 212. The foldable portions may be pivotably attached by a living hinge or other conventional pivotable connection. The second body portion 210 has a second attachment collar portion 216 and a second foldable portion 218 that is pivotable with respect to the second attachment collar portion 216.

The injection port adapter 200 may be formed of any suitable material, such as polypropylene. The adapter may be formed by any conventional manufacturing method, including injection molding and the like.

To utilize the injection port adapter 200 of this exemplary embodiment of the invention, the first and second body portions 208, 210 are assembled together so that the first and second attachment collar portions 212, 216 form an attachment collar 220 surrounding the barrel 32 of the syringe 20. Preferably, the pieces have conventional snap fasteners so that they may be snapped together. Other suitable fastening methods known to those skilled in the art can also be used. This assembly may be done by the end user of the device. During the assembly process so far, the sterility cap 28 of the syringe 20 does not need to be removed, thereby minimizing potential contamination of the cannula 22.

Figure 9:
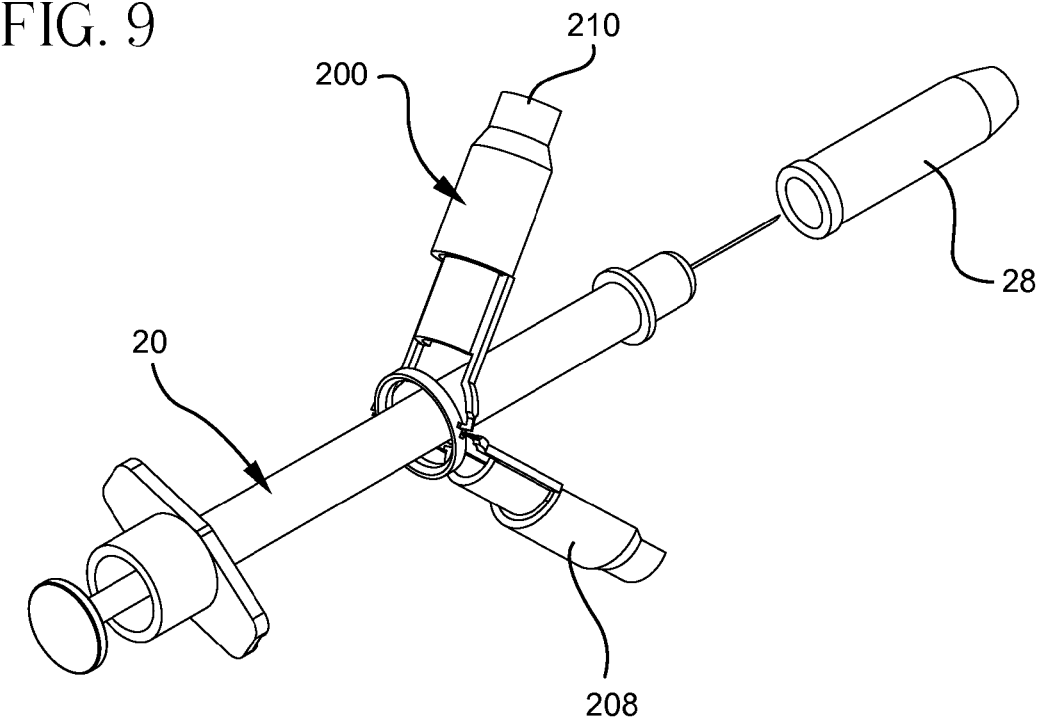
FIG. 9 is a perspective view of the syringe and the injection port adapter of FIG. 8, with the sterility cap of the syringe removed.
Figure 10:
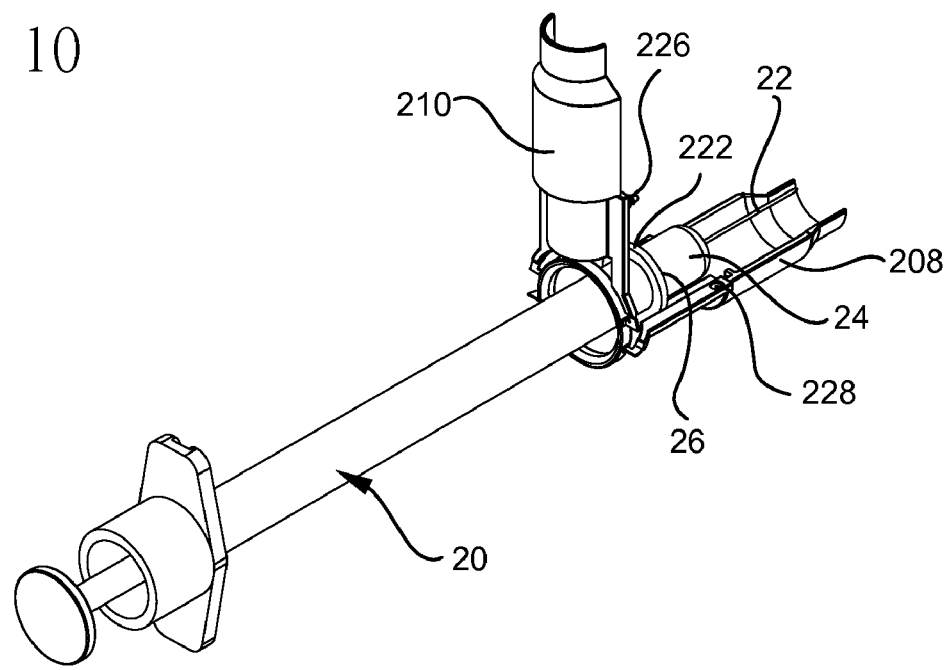
FIG. 10 is a perspective view of the syringe and the injection port adapter of FIG. 8, with the adapter in an open position on the end of the syringe.
Figure 11:
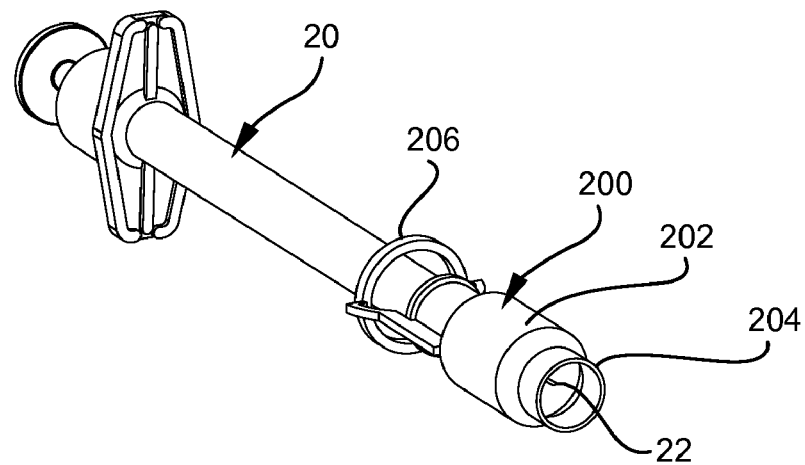
FIG. 11 is a perspective view of the syringe and the injection port adapter of FIG. 8, with the adapter in a closed position on the end of the syringe.
Figure 12:
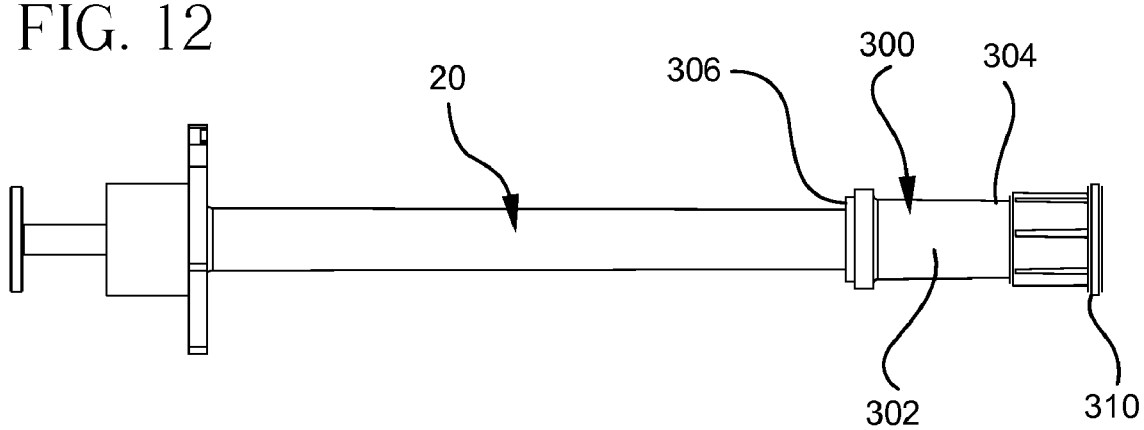
FIG. 12 is a front view of a syringe and an injection port adapter according to another exemplary embodiment of the present invention.
Figure 13:
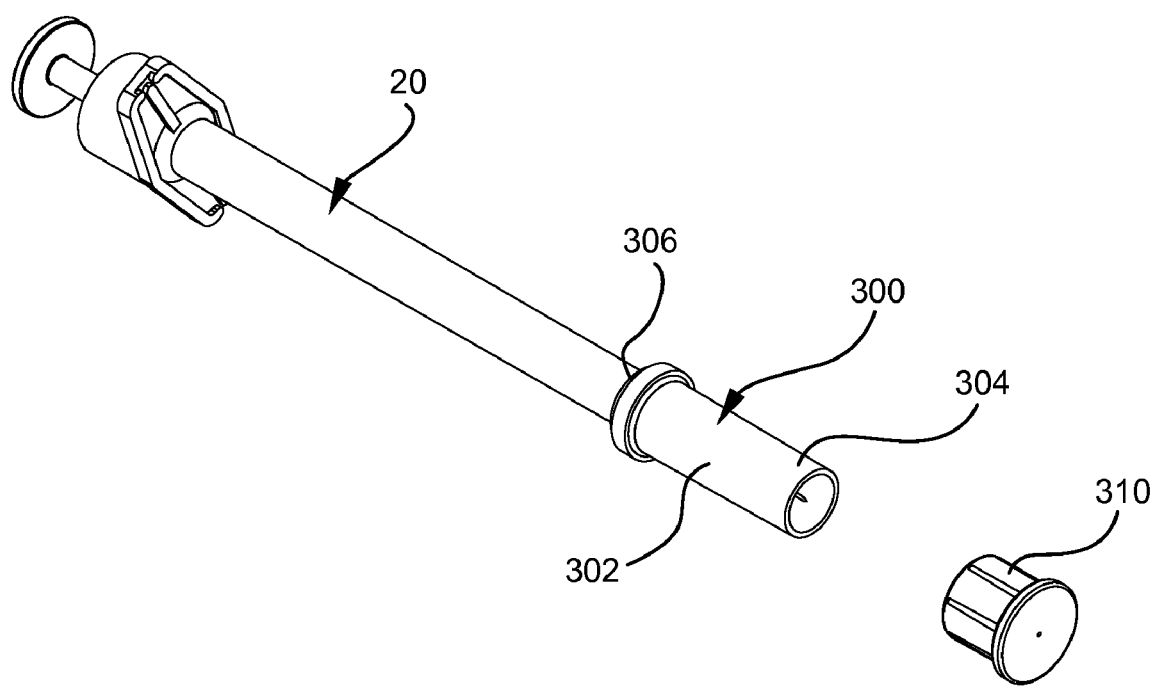
FIG. 13 is a perspective view of the syringe and the injection port adapter of FIG. 12, with the sterility cap removed.
Figure 14:
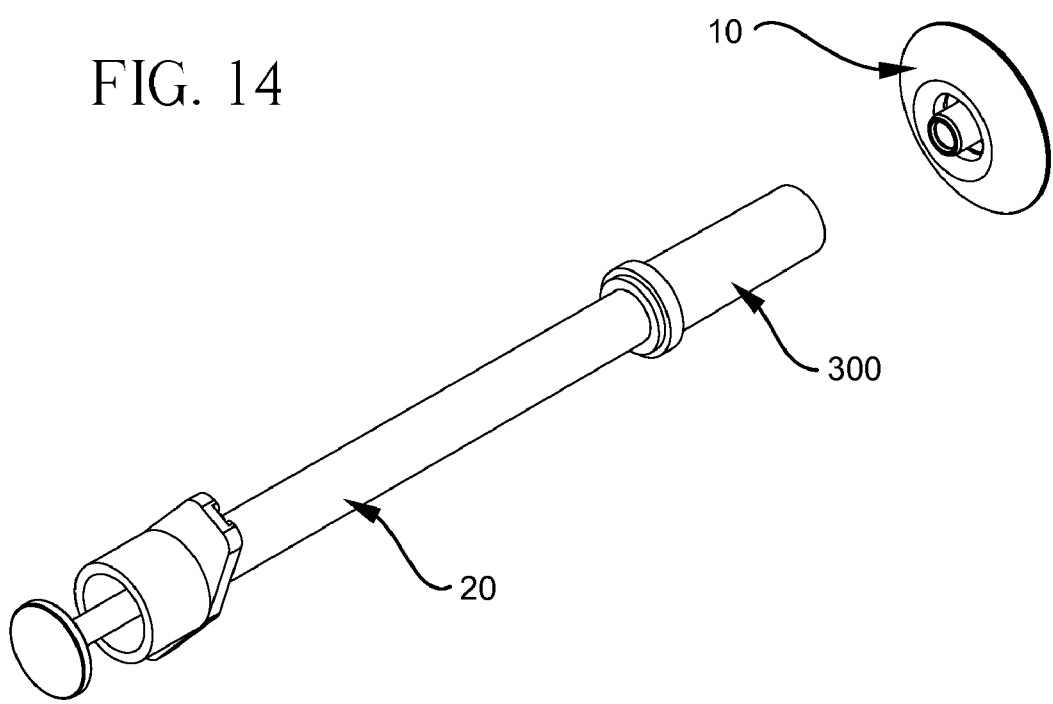
FIG. 14 is a perspective view of the syringe and the injection port adapter of FIG. 12, approaching an injection port.

Once the first and second body portions 208, 210 have been assembled together, the sterility cap 28 may be removed from the syringe 20, as shown in FIG. 9. Next, the first and second body portions 208, 210 may be slid towards the end of the syringe. The first and second body portions 208, 210 have recesses 222 for accommodating the annular flange 26 on the hub 24 of the syringe 20. At this time, one of the foldable portions 214 or 216 is placed at the proper location on the syringe 20 so that the annular flange 26 is disposed in the corresponding recess 222 of the foldable portion. The other foldable portion 214 or 216 is then folded together to close the portions around the syringe 20 and form the adapter. A fastener, such as a snap style fastener using pins 226 that extend through corresponding apertures 228, may be provided to hold the foldable portions closed with respect to one another.

The syringe 20 and the injection port adapter 200 may now be used to inject a therapeutic substance through an injection port. It should be noted that once the adapter has been placed on the syringe, it may be difficult or even impossible to load the syringe 20 using a vial because the cannula 22 is shrouded by the injection port adapter 200. Therefore, the syringe may be loaded prior to sliding the first and second body portions 208, 210 towards the end of the syringe, as mentioned above. Alternatively, a vial adapter (see FIGS. 38-42) may be provided to facilitate loading the syringe from a vial. Further details regarding such an adapter will be discussed below.

Figure 15:
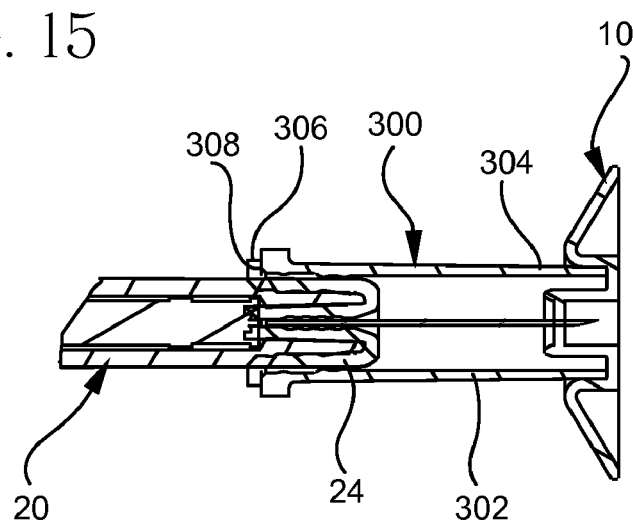
FIG. 15 is a sectional view of the end of the syringe and the injection port adapter of FIG. 12 in place on an injection port

FIGS. 12-15 show a syringe 20 and an injection port adapter 300 in accordance with another exemplary embodiment of the present invention. The injection port adapter 300 of this exemplary embodiment includes a hollow body 302 with a first end 306 and a second end 304. The first end 306 of the hollow body has an opening 308 for receiving the end of the syringe 20. As seen in FIG. 15, the syringe 20 may have a hub portion 24 as previously discussed, and the first end 306 of the hollow body 302 may mate with the hub portion 24 of the syringe 20. The second end 304 of the hollow body 302 has a geometric configuration that engages the mating portion of the injection port.

A cap 310 is provided to cover the second end 304 of the adapter 300. The cap 310 preferably seals tightly with the second end 306 of the injection port adapter 300 so that the sterility of the cannula of the syringe 20 is maintained. Thus, the injection port adapter 300 and the associated cap 310 may be used to replace a conventional sterility cap. That is, the adapter 300 may serve as both a sterility cap and an integrated adapter.

The adapter may be formed of any suitable material, such as polypropylene. The adapter may be formed by any conventional manufacturing method, including injection molding and the like.

Typically, the injection port adapter 300 of this exemplary embodiment of the invention is delivered to an end user already installed on the syringe 20. To use the adapter 300, a user removes the sterility cap 310 to expose the end of the adapter 300. If the syringe 20 is not pre-loaded, the user then loads the syringe 20 with a dose of a therapeutic substance. This may be done using a vial adapter, which is discussed below. The loaded syringe 20 and the attached adapter 300 are then brought to the injection port, the second end 304 of the adapter 300 is brought into engagement with the mating portion of the injection port 10, and the injection is made. After the injection, the syringe and the associated adapter will typically be disposed of for health and safety reasons.

FIGS. 16-21 show a syringe and an injection port adapter 400 in accordance with another exemplary embodiment of the present invention. The injection port adapter 400 of this exemplary embodiment includes a hollow body 402 with a first end 406 and a second end 404. The hollow body 402 has a first body portion 408 and a second body portion 410. The first and second body portions are pivotable with respect to one another, preferably by a living hinge.

The first body portion 408 has a first attachment collar portion 412 and a first foldable portion 414 that is pivotable with respect to the first attachment collar portion 412. Preferably, the first and second body portions are connected by a living hinge. The second body portion 410 has a second attachment collar portion 416 and a second foldable portion 418 that is pivotable with respect to the second attachment collar portion 416.

Figure 16:
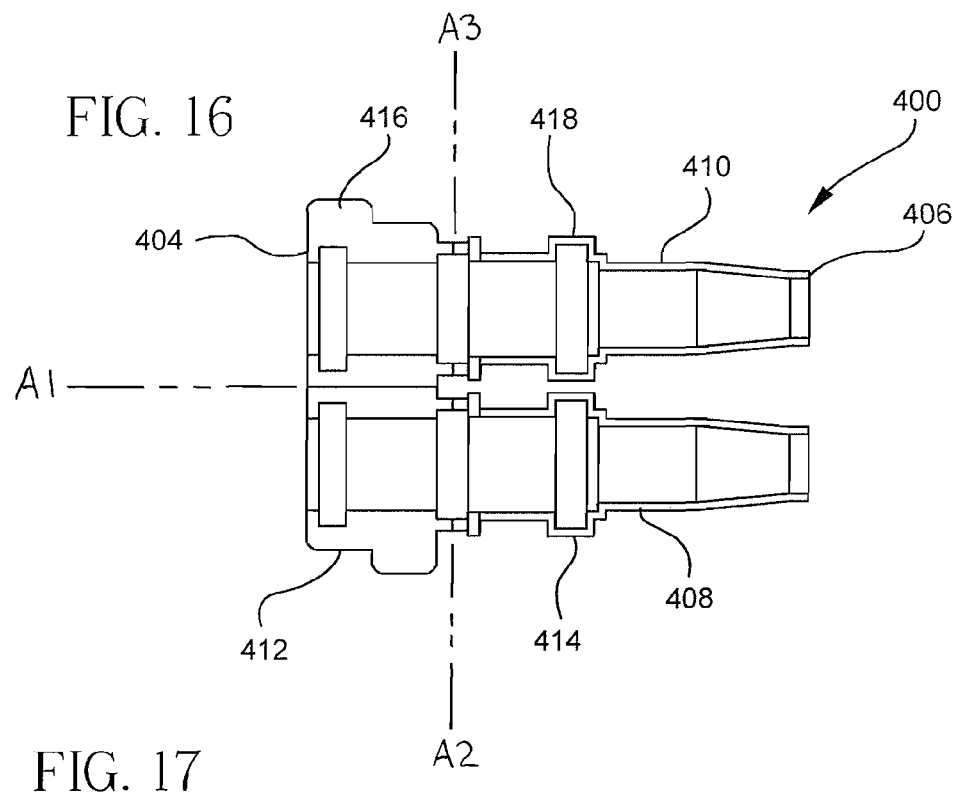
FIG. 16 is an injection port adapter for a syringe according to another exemplary embodiment of the present invention.
Figure 17:
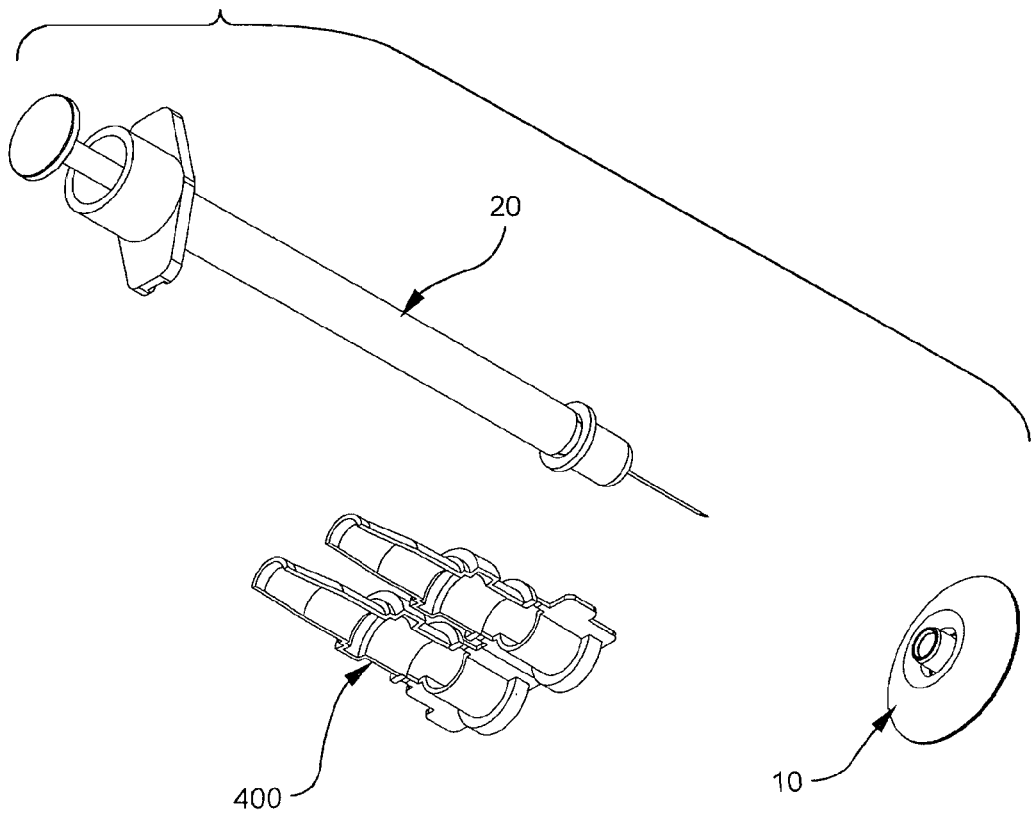
FIG. 17 is a perspective view of the injection port adapter of FIG. 16 and a syringe and an injection port.
Figure 18:
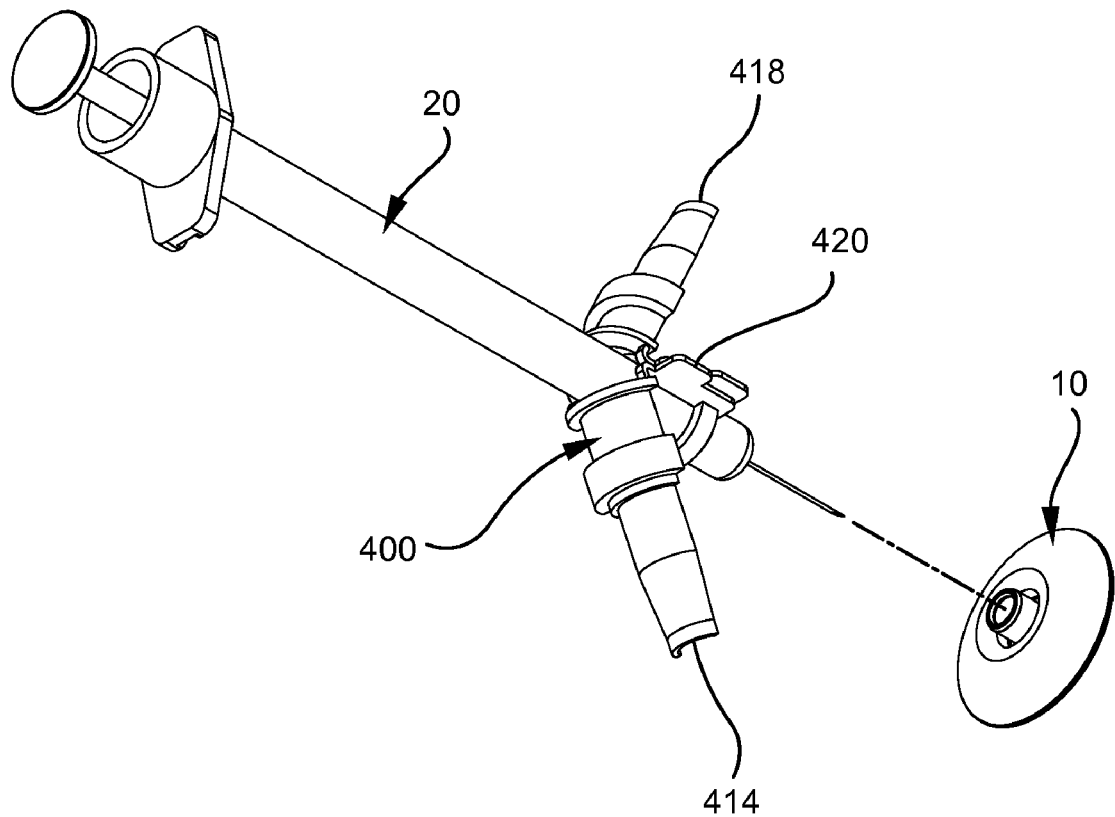
FIG. 18 is a perspective view of the injection port adapter of FIG. 16 partially installed on a syringe.
Figure 21:
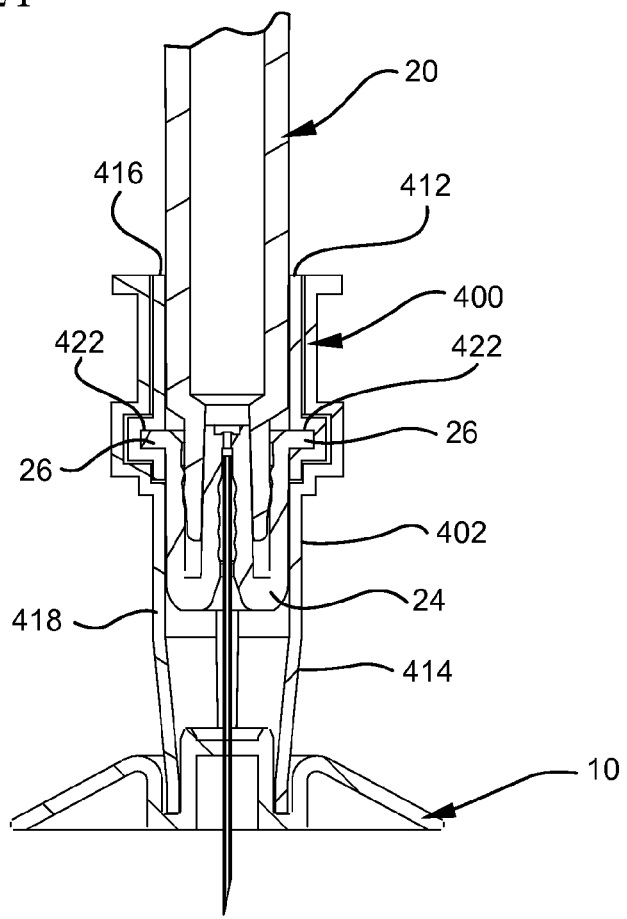
FIG. 21 is a sectional view of the end of the syringe and the injection port adapter of FIG. 16 in place on an injection port.
Figure 22:
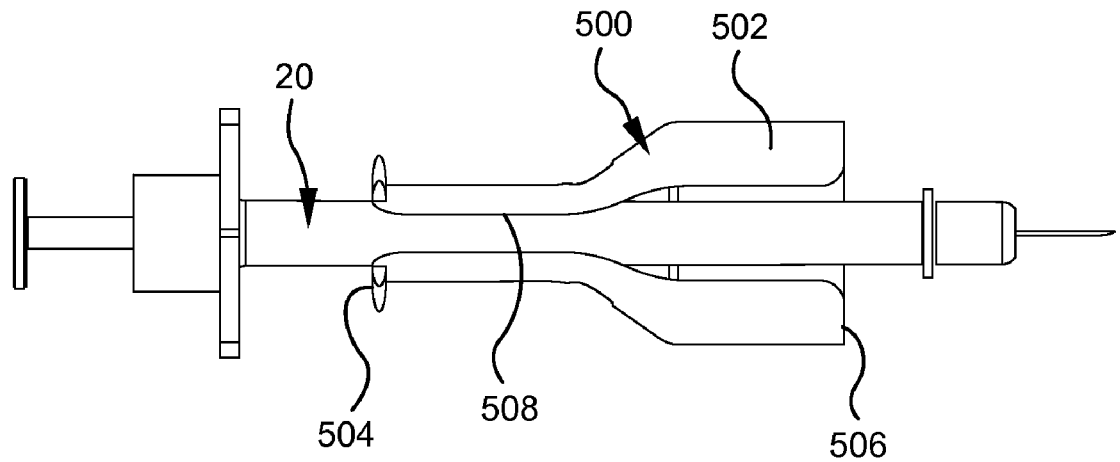
FIG. 22 is a front view of a syringe and an injection port adapter according to another exemplary embodiment of the present invention.
Figure 23:
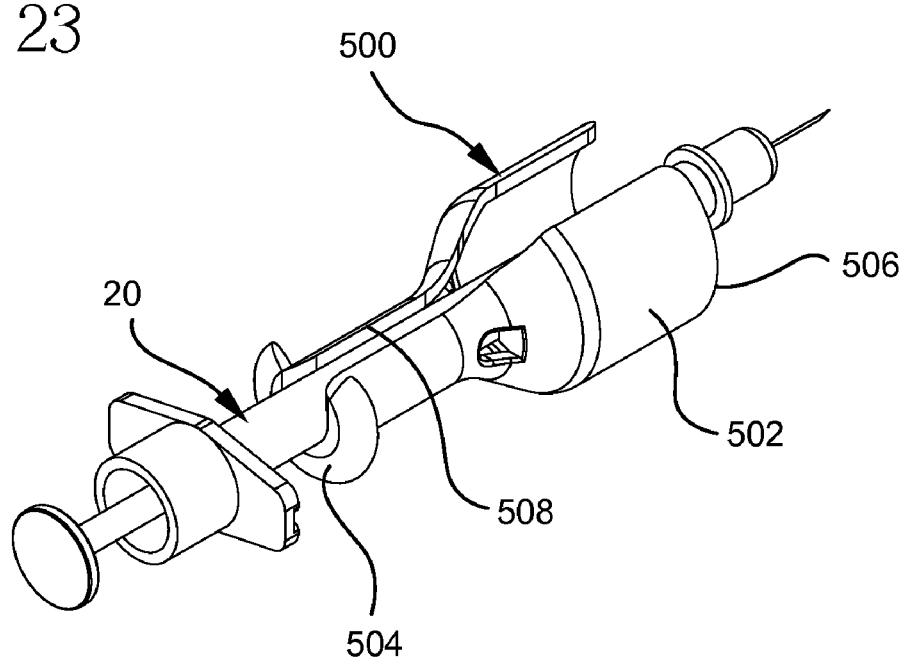
FIG. 23 is a perspective view of the syringe and injection port adapter of FIG. 22.
Figure 24:
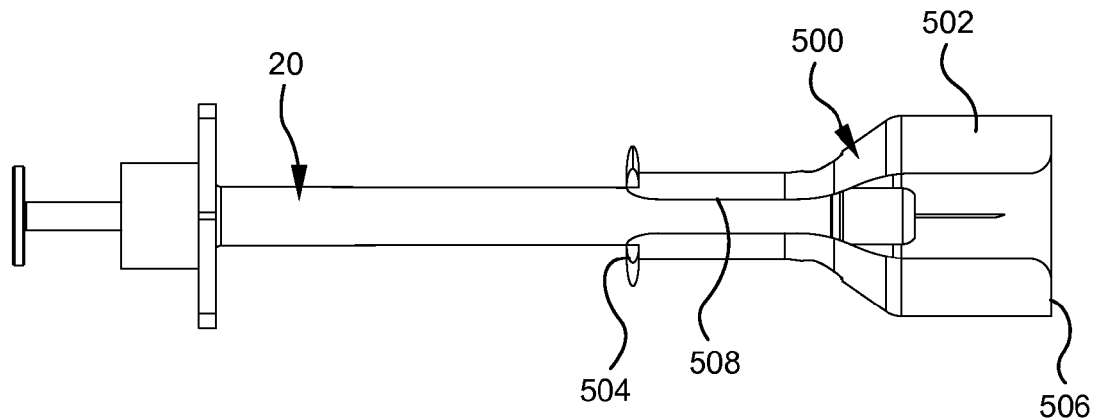
FIG. 24 is a front view of the syringe and injection port adapter of FIG. 22, with the injection port adapter placed on the end of the syringe.

The adapter 400 of this exemplary embodiment of the invention is preferably formed in a flattened state, as shown in FIG. 16, by injection molding or the like. To install the adapter 400 on a syringe 20, the flattened adapter is placed adjacent to the syringe. The first and second attachment collar portions 412, 416 have recesses 422 for accommodating the annular flange 26 on the hub 24 of the syringe 20. These recesses 422 are aligned with the annular flange 26 on the hub 24 of the syringe 20, and the first and second body portions 408, 410 are folded together about a first axis A1 so that the first and second attachment collar portions 412, 416 form an attachment collar 420 around the hub 24 of the syringe 20, as shown in FIGS. 16 and 21. Preferably, the pieces have conventional snap fasteners so that they may be snapped together. Other suitable fastening methods known to those skilled in the art can also be used. During this assembly process, the area where the adapter 400 contacts the syringe 20 extends back and away from the cannula, thereby minimizing the potential of contamination. At this time, the cannula 22 of the syringe 20 is exposed, and the syringe 20 may be loaded with a therapeutic substance from a vial.

Figure 19:
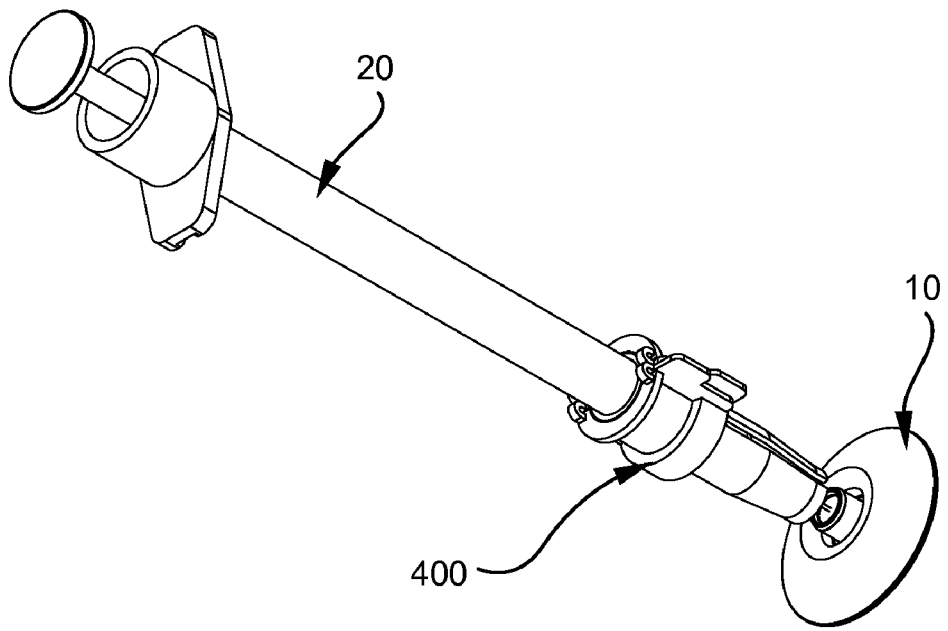
FIG. 19 is a perspective view of the injection port adapter of FIG. 16 installed on a syringe.
Figure 20:
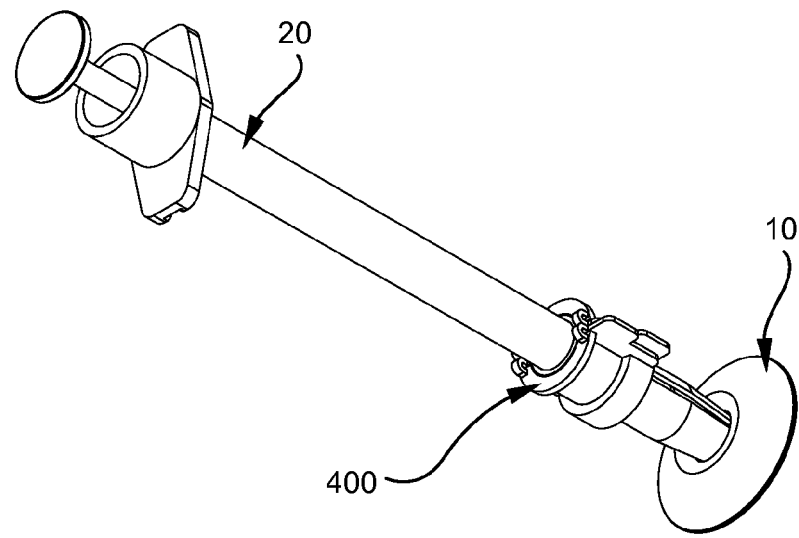
FIG. 20 is a perspective view of the injection port adapter of FIG. 16 installed on a syringe and placed on an injection port.

After the syringe is loaded, the first and second foldable portions 414, 418 are folded back about second and third axes A2 and A3 to form the hollow body 402 of the adapter 400, as shown in FIGS. 16 and 19. Preferably, the pieces have conventional snap fasteners so that they may be snapped together. Other suitable fastening methods known to those skilled in the art can also be used. With this configuration, the cannula 22 is shrouded and recessed for safety. Preferably, the injection port adapter 400 is assembled to the syringe 20 by the end user of the device.

The syringe 20 and the injection port adapter 400 may now be used to inject a therapeutic substance through an injection port. The process is substantially the same as discussed above, and thus will not be repeated.

FIGS. 22-26 show a syringe 20 and an injection port adapter 500 in accordance with another exemplary embodiment of the present invention. The injection port adapter 500 of this exemplary embodiment includes a hollow body 502 with a first end 504 and a second end 506. The hollow body 502 is a unitary, one-piece adapter. A slit 508 is formed along one side of the hollow body. The slit 508 allows the hollow body 502 to flex so that a syringe 20 may be passed through the slit 508 so that the body 502 accommodates the syringe 20.

Figure 25:
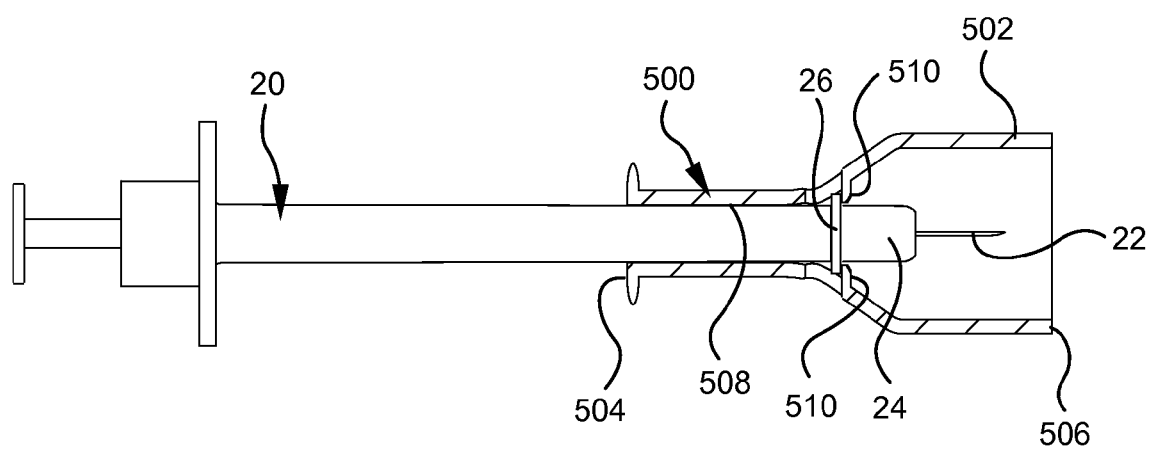
FIG. 25 is an enlarged schematic view of the syringe and injection port adapter of FIG. 22.
Figure 26:
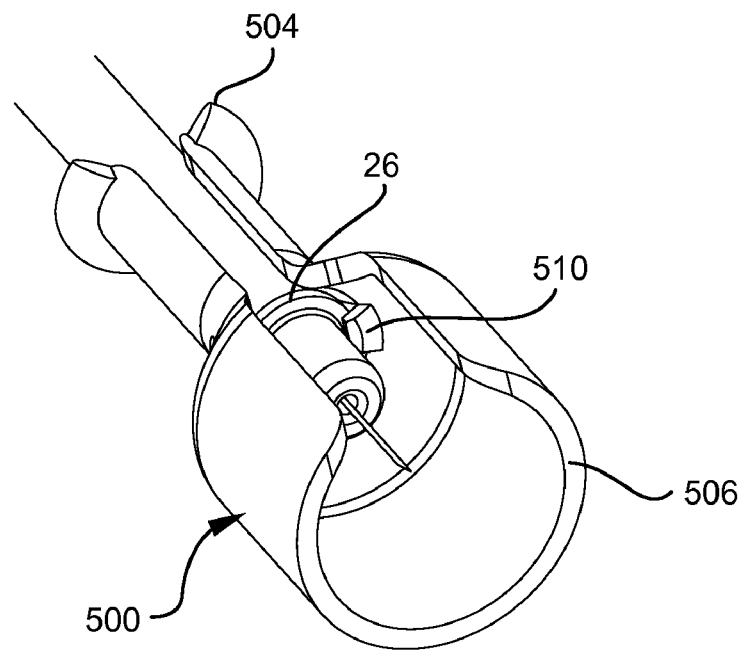
FIG. 26 is an enlarged perspective view of the interior of the injection port adapter of FIG. 22.
Figure 27:
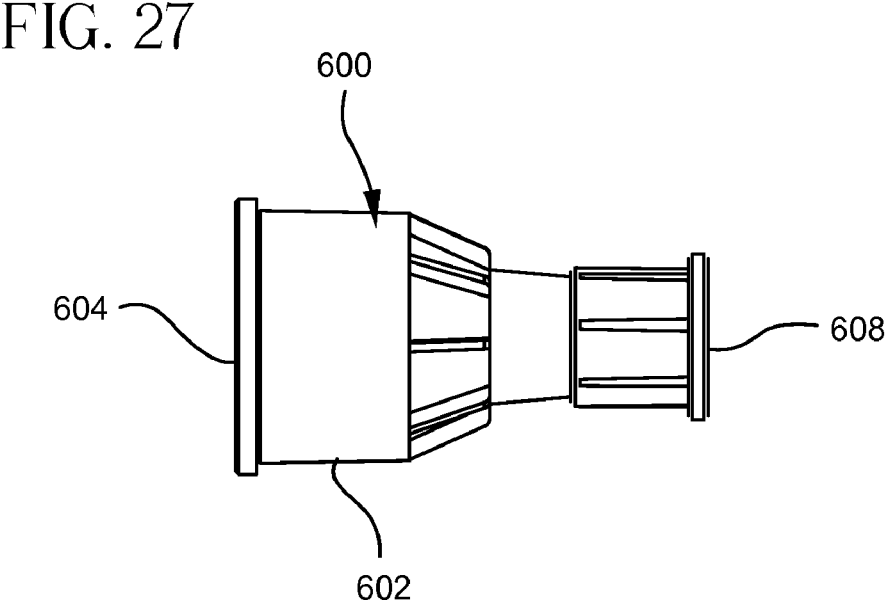
FIG. 27 is a front view of an injection port adapter for use with a pen style injection device according to another exemplary embodiment of the present invention.
Figure 28:
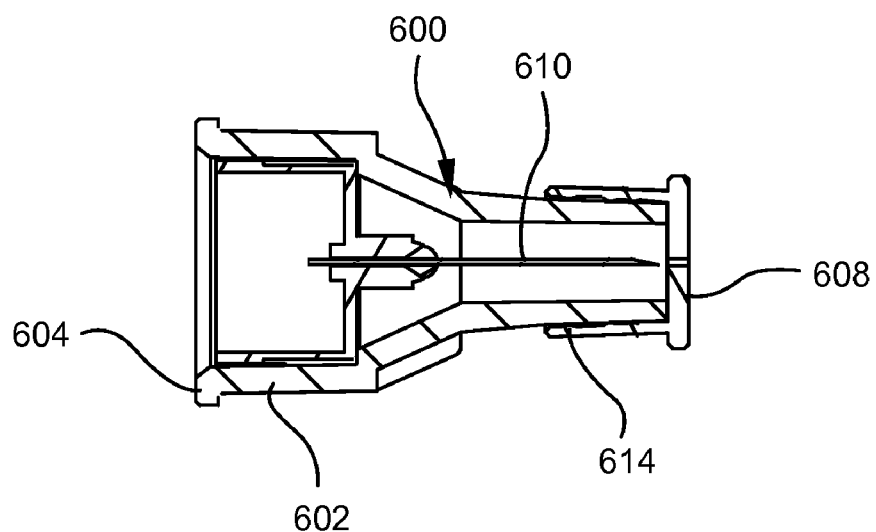
FIG. 28 is an enlarged sectional view of a portion of the injection port adapter of FIG. 27.
Figure 29:
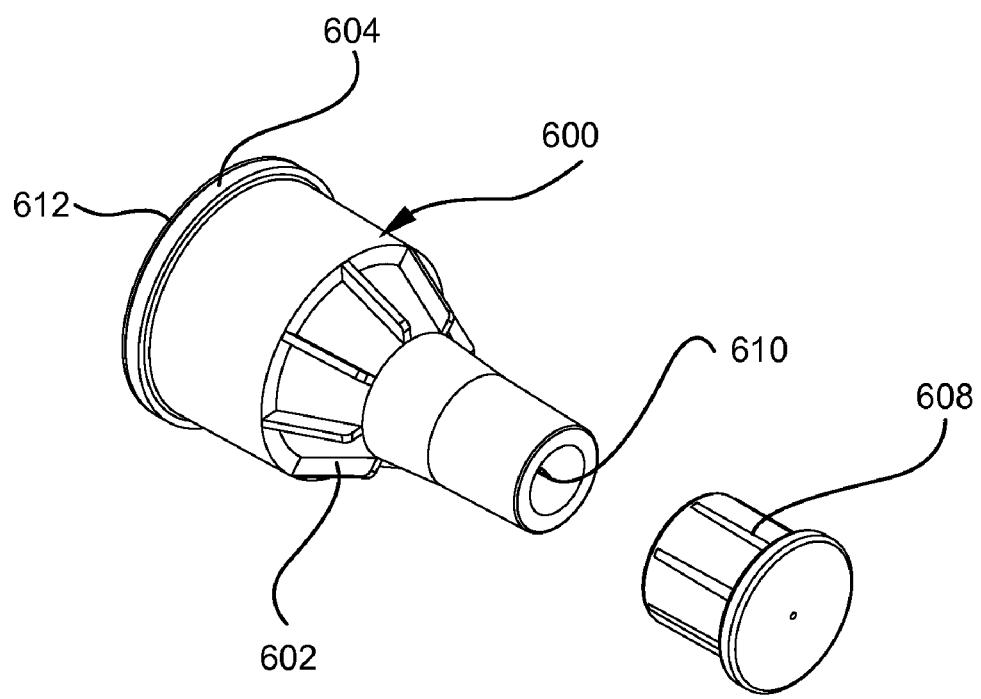
FIG. 29 a front view of an injection port adapter of FIG. 27, with the sterility cap removed.
Figure 30:
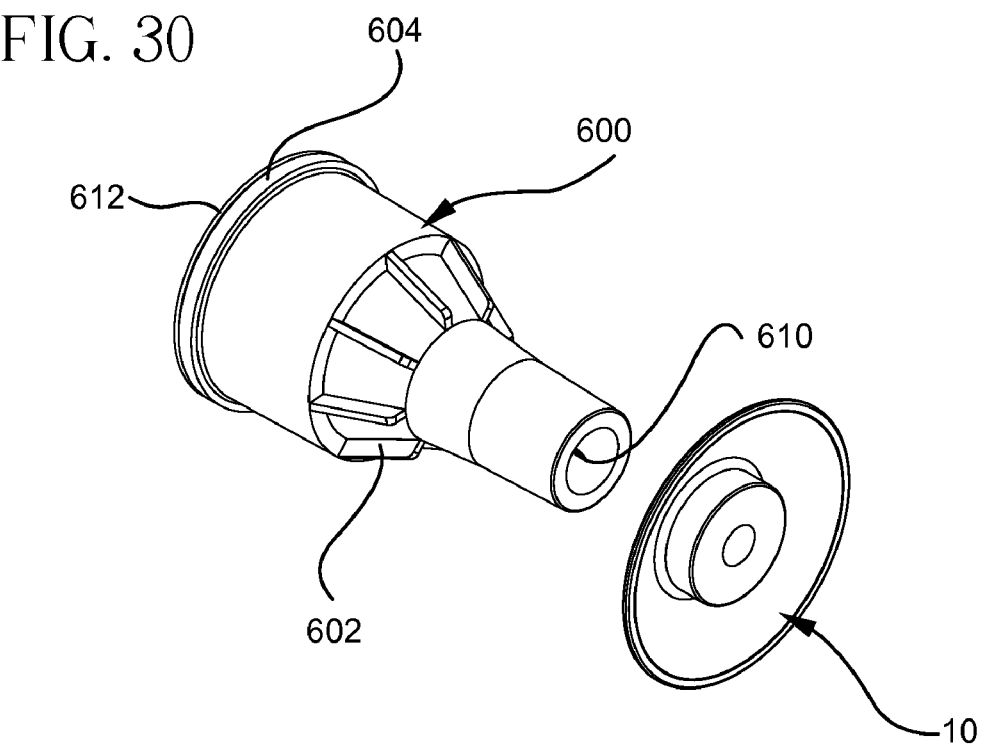
FIG. 30 is a schematic view of the injection port adapter of FIG. 27, approaching an injection port.
Figure 31:
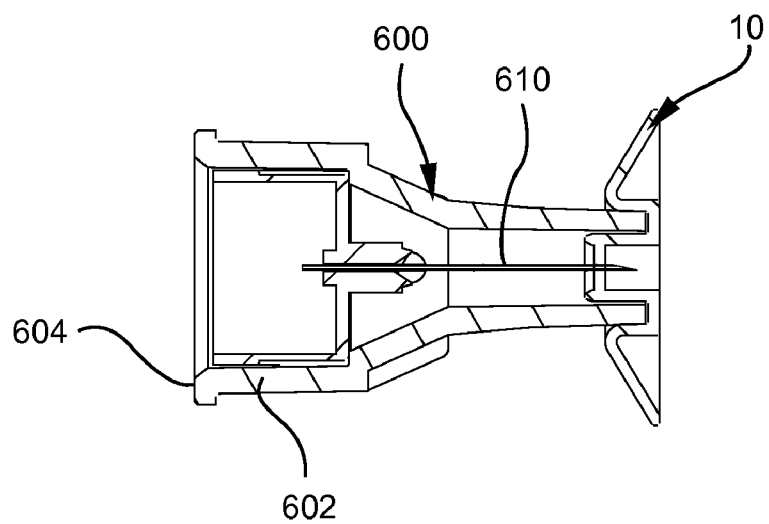
FIG. 31 is a section view of the injection port adapter of FIG. 27.

To use the adapter 500, a user places the adapter on a syringe 20 by pressing the syringe 20 through the slit 508 in the body of the adapter. Preferably, the adapter 500 is loaded on the middle portion of the syringe (that is, the position shown in FIGS. 22 and 23). After the adapter is in place, the user may remove the sterility cap from the syringe 20 and load the syringe with a therapeutic substance. Since the adapter is located away from the end of the syringe, it does not interfere with the dosing of the syringe. Once the syringe has been loaded, the user slides the adapter 500 down the barrel of the syringe 20 until the hub 24 engages the body of the adapter, as shown in FIG. 25. The adapter is now in the proper position for use. To assure that the adapter 500 does not slide back up the barrel of the syringe, the adapter may include locking features, such as a locking tab 510, to engage the hub 24 of the syringe 20.

Once the therapeutic substance has been removed, the adapter 500 may be removed from the syringe by squeezing the tip of the adapter, which causes enough deformation to disengage the locking features of the adapter 500 from the syringe. To facilitate removal, gripping features, such as wings, may be provided on the adapter. Once removed, the adapter 500 may be reused or it may be discarded.

In the above descriptions, the exemplary embodiments of the injection port adapters have been described in connection with a conventional, syringe style injection device. The injection port adapters are not limited to syringe style injection devices, however, and may be used with alternative injection devices, such as pen style injection systems. One such pen style injection system is described in U.S. Pat. No. 5,941,857, which is hereby incorporated by reference in its entirety.

FIGS. 27-31 show a pen needle with an integrated injection port adapter 600 which is suitable for use with a pen needle delivery system according to an exemplary embodiment of the present invention. The adapter 600 has an outer shield 602, a sterility cap 608, a pen needle assembly 610 (which may be, for example, a 12.5 mm assembly), and a foil or paper sterility barrier 612. The outer shield 602 has a first end 604 and a second end 606. The sterility cap 608 has, for example, three annular rings 614 similar to those used in a syringe sterility cap and is placed over the second end of the outer shield to form a sterile barrier. The foil or paper sterility barrier 612 is placed over the opening in the first end 604 of the outer shield 602 to maintain a sterile environment within the pen needle. The opening of the first end 604 of the outer shield 602 is configured to mate with a pen delivery system, such as with threads.

To use the adapter 600, the foil or paper sterility barrier 612 is peeled off, and the outer shield 602 is attached to a delivery pen, such as by screwing it onto the delivery pen. The sterility cap 608 is removed from the second end 606 of the outer shield 602 to expose the shielded needle assembly 610. The second end 606 of the outer shield 602 has a geometry that mates with the mating portion 30 of the injection port 10, as discussed above. Thus, the adapter 600 assures that the needle is properly aligned with the septum of the injection port 10 and that the needle is not inserted too far into the injection port. Once the therapeutic substance has been delivered through the injection port 10, the adapter may be removed from the delivery pen and discarded. Before removal, the sterility cap 608 may be placed back onto the adapter 600. Because the needle is covered, however, it is safe to dispose the pen needle and shield assembly without replacing the sterility cap 608.

Figure 32:
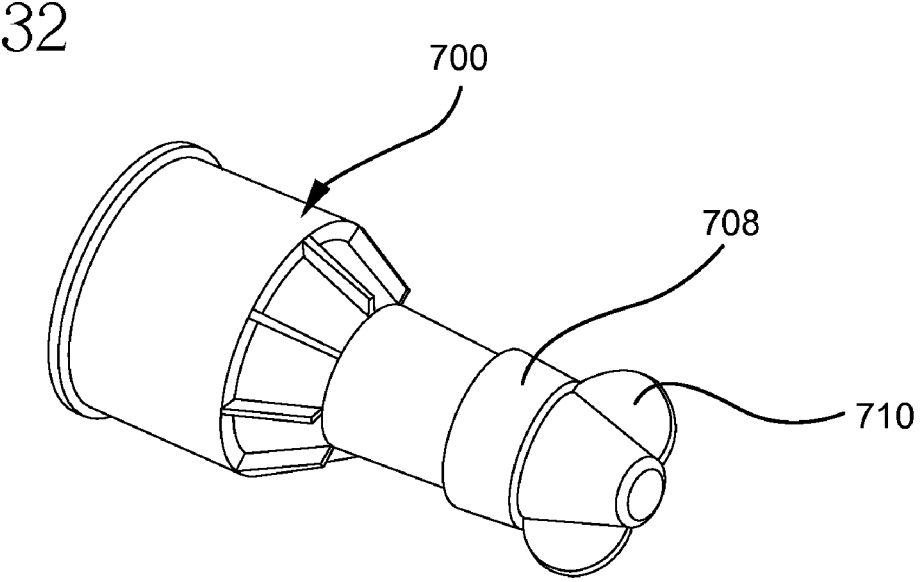
FIG. 32 is a perspective view of another embodiment of an injection port adapter for use with a pen style injection device.
Figure 33:
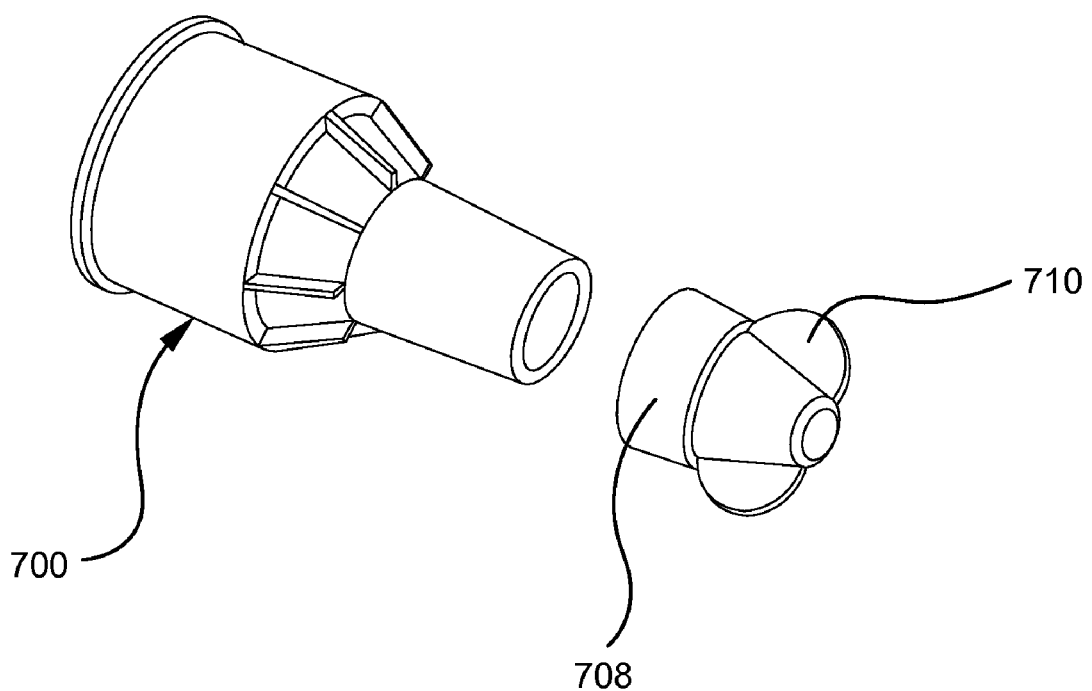
FIG. 33 is a perspective view of the injection port adapter of FIG. 32, with the sterility cap removed.
Figure 34:
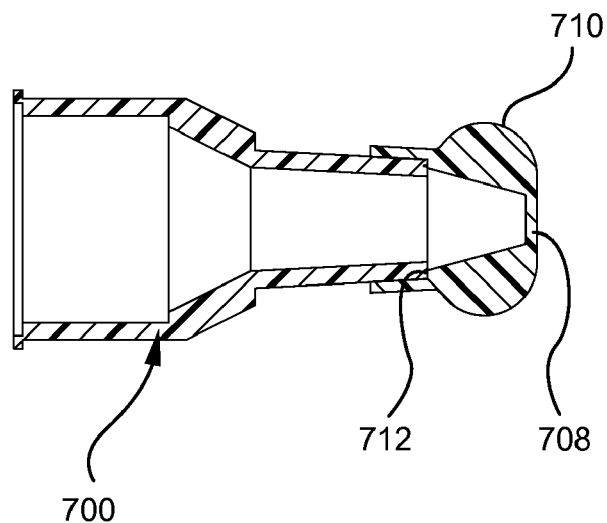
FIG. 34 is a sectional view of the injection port adapter of FIG. 32.

FIGS. 32-34 show a pen needle with an integrated injection port adapter 700 which is suitable for use with a pen needle delivery system according to another exemplary embodiment of the present invention. With the exception of the sterility cap 708, this embodiment of the invention is substantially identical to the just described embodiment. In this embodiment, the sterility cap 708 of the invention has a pair of outer wings 710 which may be used as an aid to remove the cap. Further, in this embodiment, the sterility cap 708 is preferably welded to the adapter 700 using an energy director ring 712 and ultrasonic or spin welding. This creates an air tight seal that is broken by a user when the cap 708 is twisted off.

Figure 35:
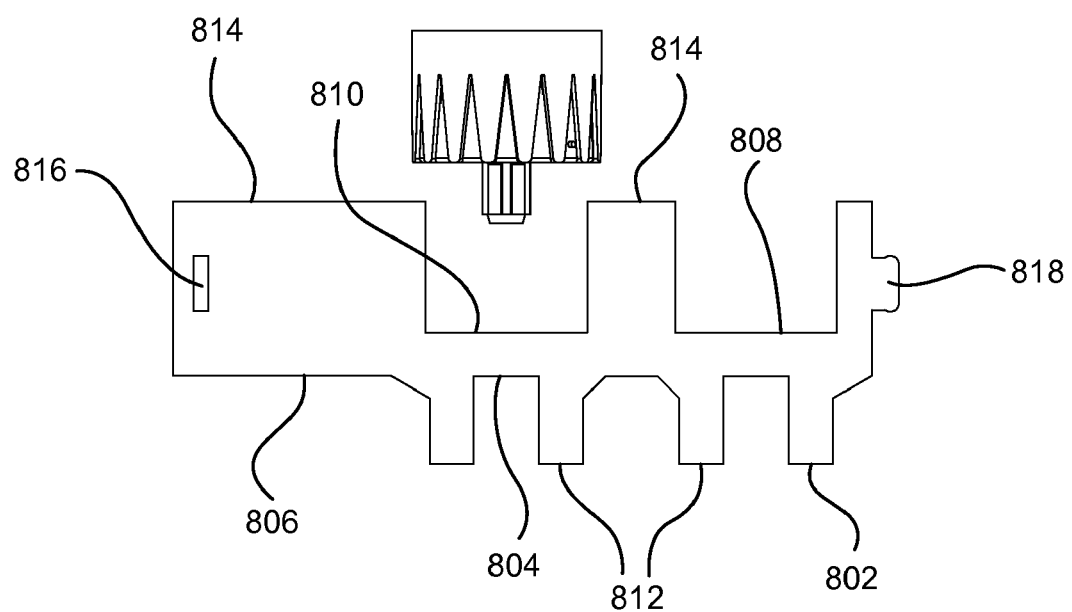
FIG. 35 is a front view of another embodiment of an injection port adapter for use with a pen style injection device, with the injection port adapter in a flattened state.
Figure 36:
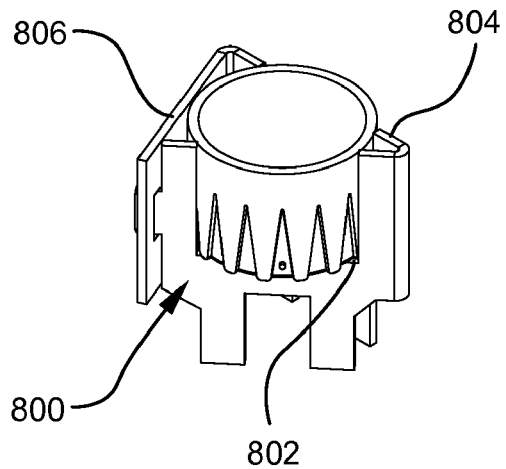
FIG. 36 is a top perspective view of the injection port adapter of FIG. 35, in a folded state, assembled with a pen style injection device.
Figure 37:
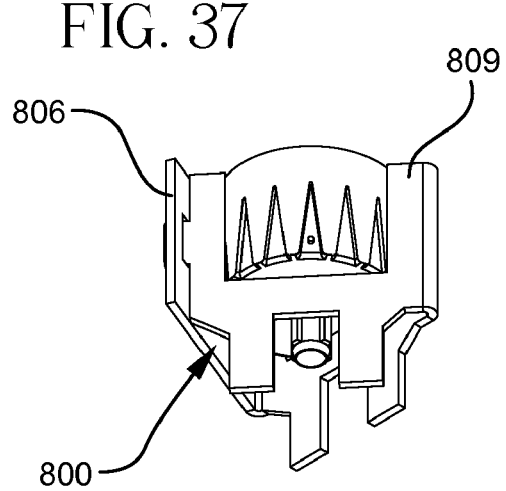
FIG. 37 is a bottom perspective view of the injection port adapter of FIG. 35, in a folded state, assembled with a pen style injection device.
Figure 38:
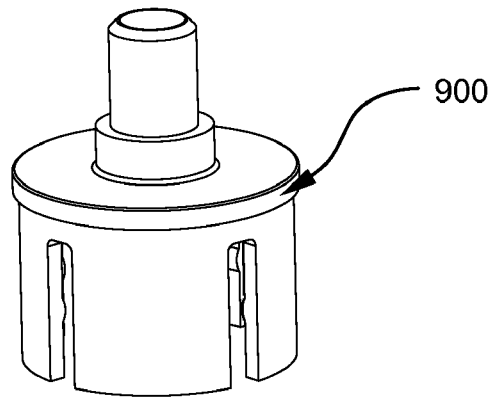
FIG. 38 is a front view of a vial adapter for using an syringe and an injection port adapter with a vial.
Figure 39:
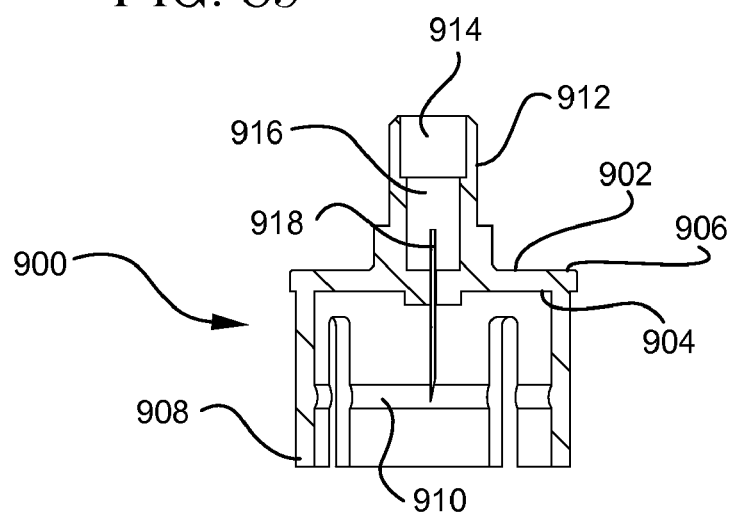
FIG. 39 is a sectional view of the vial adapter of FIG. 38.
Figure 40:
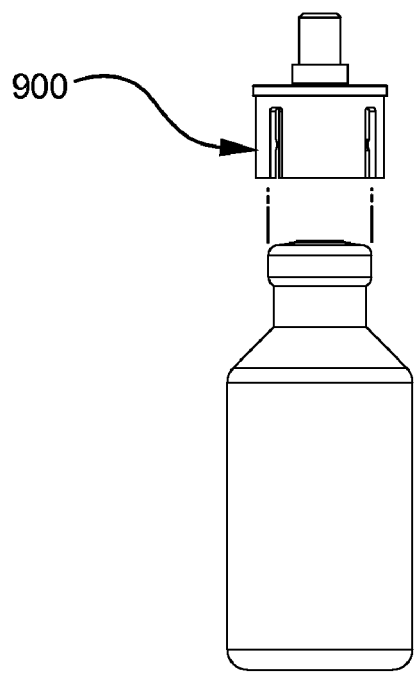
FIG. 40 is a front view of the vial adapter of FIG. 38 in the process of being placed on a vial.

FIGS. 35-37 show an adapter 800 for using a conventional pen needle assembly with an injection port 10 according to another exemplary embodiment of the present invention. The adapter 800 has first, second, and third legs 802, 804, and 806 that are connected together to form a triangular shaped body 809. The first and second legs of the adapter have first and second recesses 808, 810, respectively, that accommodate a pen needle assembly. The first and second legs of the hollow body also have extending struts 812 that are arranged in a geometric pattern that corresponds to the shape of the mating portion of an injection port when the adapter 800 is folded. In this manner, the struts 812 engage the mating portion 30 of the injection port 10 to accurately position the needle of the pen needle assembly.

Preferably, the adapter is formed in a flat pattern to minimize packaging space. To do so, the first and second legs may be connected by a living hinge 814, and the second and third legs may be connected by another living hinge 814. The ends of the first and third legs have a slot 816 and complementary tab 818. With this configuration, a user may fold the three legs into a triangular shape and fasten the legs together. The adapter may be formed of any suitable material, such as polypropylene. The adapter may be formed by any conventional manufacturing method, including injection molding and the like.

As mentioned above, with certain exemplary embodiments of the present invention, it may be difficult or even impossible to load a syringe from a vial once the adapter is placed onto the syringe. To overcome this difficulty, an adapter 900 for a vial may be provided. An exemplary embodiment of such an adapter 900 is shown in FIGS. 38-42. The adapter 900 has a disc portion 902 with a bottom surface 904 and a top surface 906. A plurality of flexible fingers 908 extend downward from the bottom surface. The flexible fingers 908 have a retention flange 910 formed on an inner surface. The flexible fingers 908 are positioned so that they accommodate the neck of a vial, and the flexibility of the flexible fingers 908 allow the retention flange 910 to pass over the crimp ring on the neck of a vial and hold the adapter in place. Furthermore, the flexibility of the flexible fingers 908 allows the vial adapter 900 to be used with a range of vial sizes.

A cylinder 912 extends from the top surface 906 of the disc 902. The cylinder 912 has an outside diameter that corresponds to the inner diameter of the above-described insulin port adapters. A septum 914 covers the opening at the top of the cylinder 912 to form a hollow cavity 916 within the cylinder 912. Preferably, the septum 914 is flush with the top edge of the cylinder to facilitate wiping the septum with an alcohol swab between uses. A cannula 918 extends through the disc 907 into the hollow cavity 916.

The first step in using the vial adapter is to place the vial adapter 900 on the vial. To do so, the flexible fingers 908 are placed over the neck and crimp ring of a vial of a therapeutic substance, and the vial adapter 900 is pressed down. The flexible fingers 908 flex outward to pass over the crimp ring. As the vial adapter 900 is pressed further down, the retention flange 910 on the inner surface of the flexible fingers 908 passes the crimp ring, and the flexible fingers 908 return to their original position so that the vial adapter is held onto the vial. Meanwhile, the cannula 918 of the vial adapter 900 is pressed through a septum on the top of the vial, thereby forming a passage between the interior of the vial and the hollow cavity 916 on the vial adapter 900.

Figure 41:
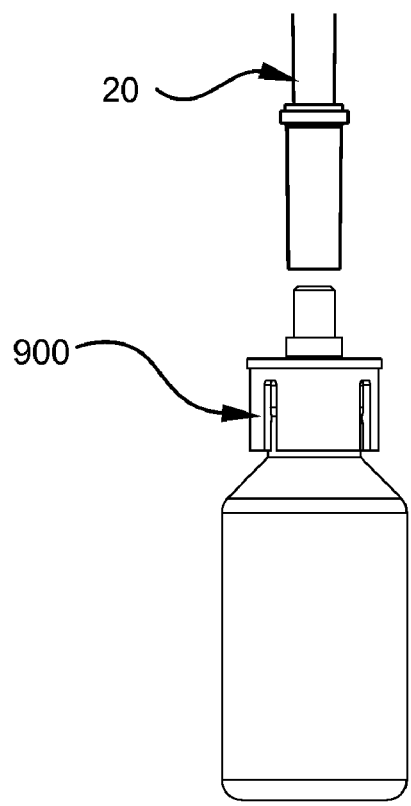
FIG. 41 is a front view of the vial adapter of FIG. 38 in place on a vial.
Figure 42:
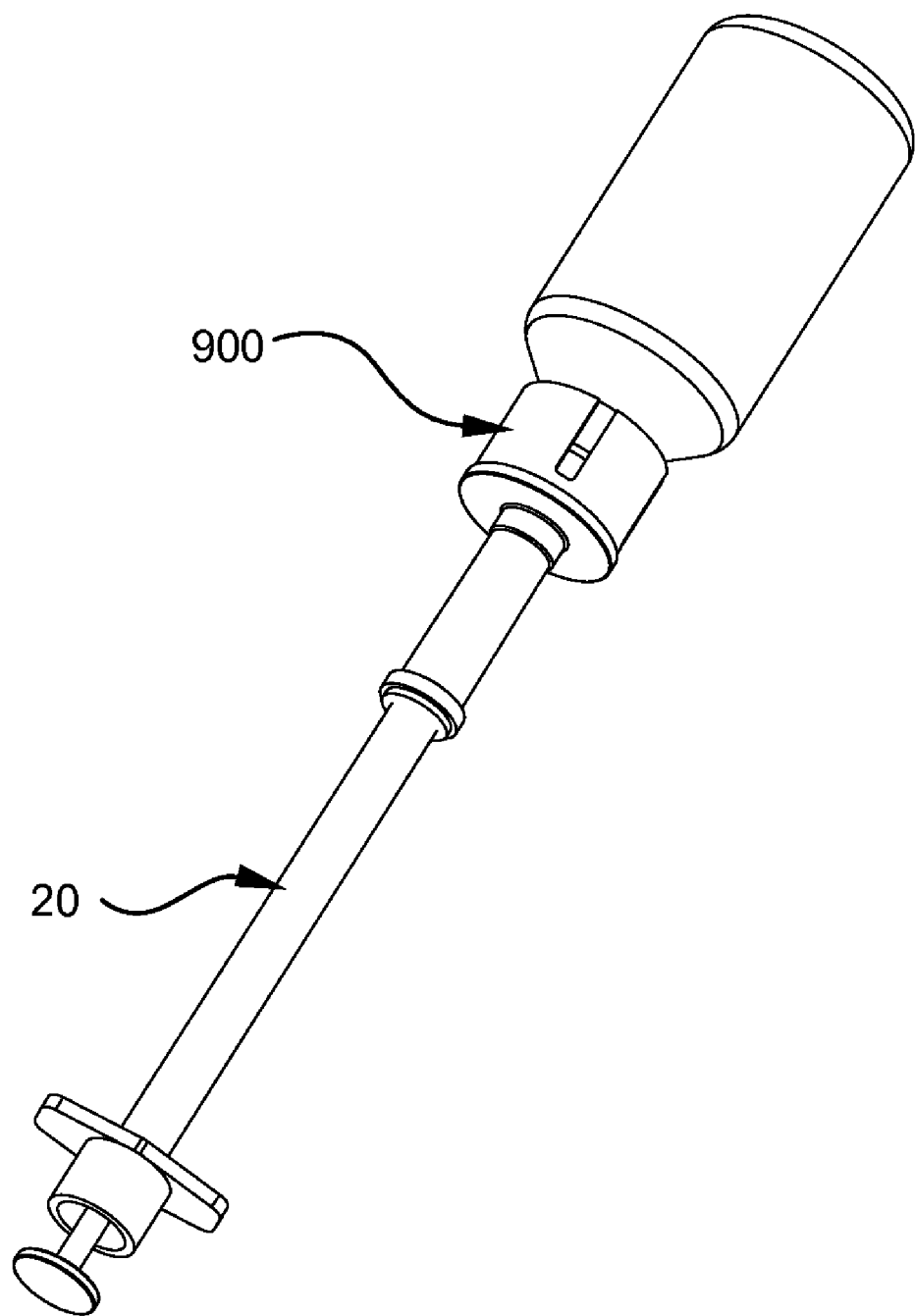
FIG. 42 is a perspective view of the vial adapter of FIG. 38 in the process of being used to load medicine in the syringe from the vial.

Once the vial adapter 900 has been placed on the vial, as shown in FIG. 41, a syringe 20 with an injection port adapter may be placed over the top cylinder 912 of the vial adapter, as shown in FIG. 42. The cannula of the syringe 20 punctures the septum 914 at the top of the vial adapter 900 and enters the cavity 916 in the vial adapter. The vial, vial adapter, and syringe are all inverted, and the syringe is operated to load the therapeutic substance into the syringe. Once the syringe is loaded, the syringe may be removed and used with an injection port in the manner described above. The vial adapter may be removed from the vial, or may be left in place for future use.

The vial adapter 900 may be formed of any suitable material, such as polypropylene. The adapter may be formed by any conventional manufacturing method, including injection molding and the like.

It should be understood that although the exemplary embodiment of the vial adapter has a cylinder for mating with an injection port adapter, the vial adapter is not limited to a cylindrical shape. Any geometric pattern that mates with the injection port adapter of a syringe is possible.

While the invention has been shown and described with reference to certain embodiments thereof, it will be understood by those skilled in the art that various changes in form and details may be made therein without departing from the spirit and scope of the invention as defined by the appended claims and their equivalents. For example, although a subcutaneous injection port has been described herein, the principles of the present invention are applicable to other types of injection ports, such as intradermal injection ports.

What is claimed is:

1. An adapter for utilizing a syringe with an injection port, comprising:
   a body having a first end and a second end, the first end of the body being adapted to receive an end of a syringe and the second end being configured to mate with an injection port, the body including:
   a first body portion having a first attachment collar portion pivotably connected to a first foldable portion; and
   a second body portion that mates with the first body portion, the second body portion having a second attachment collar pivotably connected to a second foldable portion, the first and second attachment collar portions mating with one another to form an attachment collar;
   wherein the first and second foldable portions are foldable between an open position and a closed position, the first and second foldable portions covering substantially an entire length of the attachment collar when in the closed position and uncovering the attachment collar when in the open position.

2. An adapter according to claim 1, further comprising a hinge connecting the first and second body portions.

3. An adapter according to claim 1, wherein the first and second body portions each have a recess adapted to receive an end of the syringe to align the syringe with the injection port.

4. An adapter according to claim 1, wherein the mated first and second body portions cover the end of the syringe when disposed thereon.

5. An adapter according to claim 1, wherein the first and second attachment collar portions are mated by snap fasteners.

6. An adapter according to claim 1, wherein the adapter is integrally formed as a single unit.

7. An adapter according to claim 1, wherein the mated first and second attachment collar portions circumferentially surround a portion of the syringe.

8. An adapter according to claim 1, wherein the mated first and second foldable portions circumferentially surround a portion of the syringe.

9. An adapter according to claim 1, wherein the first and second body portions cover an end of a cannula of the syringe when in the closed position.

10. An adapter for utilizing a syringe with an injection port, comprising:
    a body having a first end and a second end, the first end of the body being adapted to receive an end of a syringe and the second end being configured to mate with an injection port, the body including:
    a first body portion having a first attachment collar portion pivotably connected to a first foldable portion;
    and a second body portion that mates with the first body portion, the second body portion having a second attachment collar pivotably connected to a second foldable portion, the first and second attachment collar portions mating with one another to form an attachment collar;
    wherein the first and second foldable portions are foldable about first and second axes between a closed position in which substantially an entire length of the attachment collar is covered by the first and second foldable portions and an open position in which the attachment collar is uncovered, and the first and second attachment collars are rotatable about a third axis, the third axis being substantially perpendicular to the first and second axes.

11. An adapter according to claim 10, further comprising a hinge connecting the first and second body portions.

12. An adapter according to claim 10, wherein the first and second body portions each have a recess adapted to receive an end of the syringe to align the syringe with the injection port.

13. An adapter according to claim 10, wherein the mated first and second body portions cover the end of the syringe when disposed thereon.

14. An adapter according to claim 10, wherein the first and second body portions cover substantially an entire length of attachment collar when in the closed position.

15. An adapter according to claim 10, wherein the attachment collar circumferentially surrounds a portion of the syringe when mated.

16. An adapter according to claim 10, wherein the first and second body portions cover an end of a cannula of the syringe when in the closed position.

17. An adapter according to claim 10, wherein a cap covers the second end of the body.

18. An adapter according to claim 10, wherein the adapter is integrally formed as a single unit.

19. An adapter according to claim 10, wherein the first and second foldable portions circumferentially surround a portion of the syringe when in the closed position.

20. An adapter according to claim 10, wherein the first and second attachment collar portions are mated by snap fasteners.

* * * * *